United States Patent [19]

Bryant et al.

[11] 4,297,239

[45] Oct. 27, 1981

[54] HYDROFORMYLATION CATALYST REACTIVATION

[75] Inventors: David R. Bryant; Richard A. Galley, both of South Charleston, W. Va.

[73] Assignee: Union Carbide Corporation, New York, N.Y.

[21] Appl. No.: 120,101

[22] Filed: Feb. 28, 1980

Related U.S. Application Data

[63] Continuation-in-part of Ser. No. 58,123, Jul. 16, 1979, abandoned.

[51] Int. Cl.$^3$ .................. B01J 31/40; B01J 31/24; C07C 45/50; B01J 31/20
[52] U.S. Cl. .................................... 252/412; 203/72; 203/91; 252/411 R; 252/414; 252/420; 252/431 P; 568/454
[58] Field of Search ............... 252/411 R, 414, 431 R, 252/428, 412, 420, 416, 431 P; 260/429 R; 203/72, 91

[56] References Cited

U.S. PATENT DOCUMENTS

| | | | |
|---|---|---|---|
| 3,527,809 | 9/1970 | Pruett | 568/454 |
| 3,547,964 | 12/1970 | Olivier et al. | 260/429 |
| 3,555,098 | 1/1971 | Olivier et al. | 568/454 |
| 3,560,539 | 2/1971 | Booth et al. | 260/429 |
| 3,641,076 | 2/1972 | Booth | 260/429 R |
| 3,857,895 | 12/1974 | Booth | 260/604 HF |
| 3,871,970 | 3/1975 | Nienburg et al. | 203/6 |
| 3,968,134 | 7/1976 | Gregario et al. | 260/429 R |
| 4,021,463 | 5/1977 | Kummer et al. | 260/429 R |
| 4,041,082 | 8/1977 | Onoda et al. | 568/454 |
| 4,060,557 | 11/1977 | Macaluso, Sr. et al. | 568/454 |
| 4,113,754 | 9/1978 | Kummer et al. | 260/429 R |
| 4,148,830 | 4/1979 | Pruett et al. | 568/454 |
| 4,151,209 | 4/1979 | Paul et al. | 568/454 |
| 4,166,773 | 9/1979 | Higley et al. | 203/72 |
| 4,196,096 | 4/1980 | Dawes et al. | 252/414 |
| 4,221,743 | 9/1980 | Halstead et al. | 568/454 |
| 4,247,486 | 1/1981 | Brewester et al. | 568/454 |
| 4,260,828 | 4/1981 | Bryant et al. | 568/454 |

FOREIGN PATENT DOCUMENTS

| | | |
|---|---|---|
| 856542 | 1/1978 | Belgium . |
| 1290535 | 3/1969 | Fed. Rep. of Germany . |
| 2044651 | 3/1972 | Fed. Rep. of Germany . |
| 1802895 | 7/1973 | Fed. Rep. of Germany . |
| 2406323 | 8/1975 | Fed. Rep. of Germany . |
| 51-23212 | 2/1976 | Japan . |
| 1128934 | 10/1968 | United Kingdom . |
| 1228201 | 4/1971 | United Kingdom . |
| 1440413 | 6/1976 | United Kingdom . |

OTHER PUBLICATIONS

*Hydrocarbon Processing*, Apr. 1970, pp. 112–114, Olivier et al.

*Primary Examiner*—P. E. Konopka
*Attorney, Agent, or Firm*—Reynold J. Finnegan

[57] ABSTRACT

Hydroformylation mediums, and a process for producing same, which are derived from a rhodium complex concentrate, as well as a hydroformylation process for producing aldehydes which employs said concentrate as a source of rhodium for the rhodium complex catalyst of said process.

54 Claims, No Drawings

HYDROFORMYLATION CATALYST REACTIVATION

This application is a continuation-in-part of our U.S. Application Ser. No. 058,123 filed July 16, 1979 now abandoned.

FIELD OF THE INVENTION

This invention relates to novel hydroformylation mediums prepared from rhodium complex concentrates containing reactivated rhodium which are derived from spent hydroformylation reaction mediums containing a partially deactivated rhodium complex catalyst and triarylphosphine. This invention also relates to an improved process for preparing aldehydes by the hydroformylation of an olefin in the presence of a rhodium complex catalyst, the improvement comprising employing as a source of rhodium for the catalyst said rhodium complex concentrate.

BACKGROUND OF THE INVENTION

Processes for forming aldehydes by the hydroformylation reaction (oxo synthesis) of an olefin with carbon monoxide and hydrogen in the presence of a rhodium complex catalyst and free triarylphosphine are well known in the art.

For instance, U.S. Pat. No. 3,527,809, the entire disclosure of which is incorporated herein, discloses a hydroformylation process where olefins are hydroformylated with carbon monoxide and hydrogen in the presence of a rhodium complex catalyst and free triarylphosphine to produce aldehydes in high yields at low temperatures and pressures, where the normal to iso-(or branch chain) aldehyde isomer ratio of product aldehydes is high.

It is also known that, under hydroformylation conditions, some of the product aldehydes may condense to form by-product, high boiling aldehyde condensation products such as aldehyde dimers or trimers. Commonly-assigned U.S. Pat. No. 4,148,830, the entire disclosure of which is incorporated herein by reference thereto, discloses the use of these high boiling liquid aldehyde condensation products as a reaction solvent for the catalyst. More specifically, as pointed out in said U.S. Pat. No. 4,148,830, some of the aldehyde product is involved in various reactions as depicted below using n-butyraldehyde as an illustration:

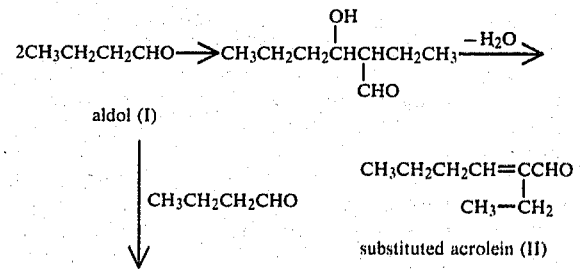

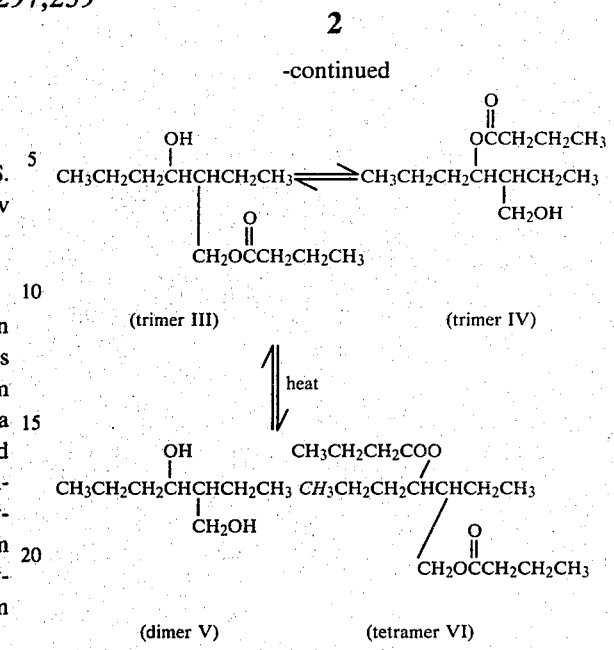

In addition, aldol I can undergo the following reaction:

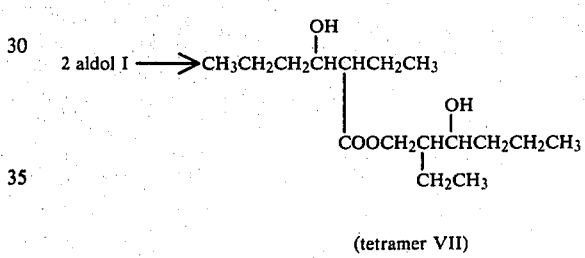

The names in parentheses in the afore-illustrated equations, aldol I, substituted acrolein II, trimer III, trimer IV, dimer V, tetramer VI, and tetramer VII, are for convenience only. Aldol I is formed by an aldol condensation; trimer III and tetramer VII are formed via Tischenko reactions; trimer IV by a transesterification reaction; dimer V and tetramer VI by a disproportionation reaction. Principal condensation products are trimer III, trimer IV, and tetramer VII, with lesser amounts of the other products being present. Such condensation products, therefore, contain substantial quantities of hydroxylic compounds as witnessed, for example, by trimers III and IV and tetramer VII.

Similar condensation products are produced by self-condensation of iso-butyraldehyde and a further range of compounds is formed by condensation of one molecule of normal butyraldehyde with one molecule of iso-butyraldehyde. Since a molecule of normal butyraldehyde can aldolize by reaction with a molecule of iso-butyraldehyde in two different ways to form two different aldols VIII and IX, a total of four possible aldols can be produced by condensation reactions of a normal/iso mixture of butyraldehydes.

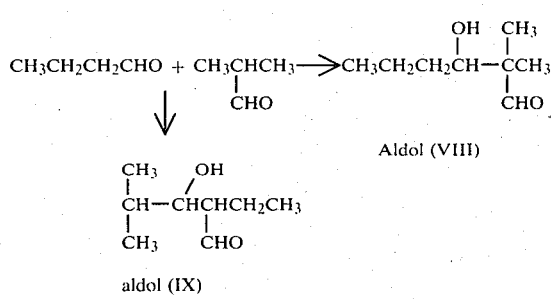

Aldol (VIII)

$$\begin{array}{c} CH_3 \quad OH \\ | \quad / \\ CH-CHCHCH_2CH_3 \\ | \quad | \\ CH_3 \quad CHO \end{array}$$

aldol (IX)

Aldol I can undergo further condensation with isobutyraldehyde to form a trimer isomeric with trimer III and aldols VIII and IX and the corresponding aldol X produced by self-condensation of two molecules of isobutyraldehyde can undergo further reactions with either normal or isobutyraldehyde to form corresponding isomeric trimers. These trimers can react further analogously to trimer III so that a complex mixture of condensation products is formed.

In addition commonly-assigned copending U.S. application Ser. No. 776,934 filed Mar. 11, 1977, now U.S. Pat. No. 4,247,486 (Belgium Patent No. 853,377), the entire disclosure of which is incorporated herein by reference thereto, discloses a liquid phase hydroformylation reaction using a rhodium complex catalyst, wherein the aldehyde reaction products and some of their higher boiling condensation products are removed in vapor form from the catalyst containing liquid body (or solution) at the reaction temperature and pressure. The aldehyde reaction products and the condensation products are condensed out of the off gas from the reaction vessel in a product recovery zone and the unreacted starting materials (e.g., carbon monoxide, hydrogen and/or alpha-olefin) in the vapor phase from the product recovery zone are recycled to the reaction zone. Furthermore, by recycling gas from the product recovery zone coupled with make-up starting materials to the reaction zone in sufficient amounts, it is possible, using a $C_2$ to $C_5$ olefin as the alpha-olefin starting material, to achieve a mass balance in the liquid body in the reactor and thereby remove from the reaction zone at a rate at least as great as their rate of formation essentially all the higher boiling condensation products resulting from self-condensation of the aldehyde product.

More specifically, according to said Ser. No. 776,934, a process for the production of an aldehyde containing from 3 to 6 carbon atoms is disclosed which comprises passing an alpha-olefin containing from 2 to 5 carbon atoms together with hydrogen and carbon monoxide at a prescribed temperature and pressure through a reaction zone containing the rhodium complex catalyst dissolved in a liquid body, continuously removing a vapor phase from the reaction zone, passing the vapor phase to a product separation zone, separating a liquid aldehyde containing product in the product separation zone by condensation from the gaseous unreacted starting materials, and recycling the gaseous unreacted starting materials from the product separation zone to the reaction zone.

It is also known in the prior art that even in the absence of intrinsic poisons there may be deactivation of rhodium hydroformylation catalysts under hydroformylation conditions. Copending, commonly-assigned U.S. patent application Ser. No. 762,336 filed Jan. 25, 1977, abandoned in favor of continuation U.S. application No. 151,293 now U.S. Pat. 4,260,828 (Belgium Patent No. 863,268), the entire disclosure of which is incorporated herein by reference thereto, indicates that the deactivation of rhodium hydroformylation catalysts under hydroformylation conditions in the substantial absence of extrinsic poisons is due to the combination of the effects of temperature, phosphine ligand: rhodium mole ratio, and the partial pressures of hydrogen and carbon monoxide and is termed an intrinsic deactivation. It is further disclosed therein that this intrinsic deactivation can be reduced or substantially prevented by establishing and controlling and correlating the hydroformylation reaction conditions to a low temperature, low carbon monoxide partial pressure and high free triarylphosphine ligand:catalytically active rhodium mole ratio.

The manner in which the caron monoxide partial pressure, temperature and free triarylphosphine:-catalytically active rhodium mole ratio should be controlled and correlated to thus limit the deactivation of the catalyst is illustrated as follows.

As an example, for the triarylphosphine ligand triphenylphosphine, the specific relationship between these three parameters and catalyst stability is defined by the formula:

$$F = 1000/(1+e^y)$$

where
F = stability factor
e = Naperian log base (i.e., 2.718281828)
$y = K_1 + K_2 T + K_3 P + K_4 (L/Rh)$
T = reaction temperature (°C.)
P = partial pressure of CO (psia)
L/Rh = free triarylphosphine:catalytically active rhodium mole ratio
$K_1 = -8.1126$
$K_2 = 0.07919$
$K_3 = 0.0278$
$K_4 = -0.01155$ As pointed out in said Ser. No. 762,336, an olefin response factor must be employed to obtain the stability factor under actual hydroformylation conditions. Olefins generally enhance the stability of the catalyst and their effect on catalyst stability is more fully explained in said application. The above relationship is substantially the same for other triarylphosphines, except that the constants $K_1$, $K_2$, $K_3$ and $K_4$ may be different. Those skilled in the art can determine the specific constants for other triarylphosphines with a minimum amount of experimentation as explained more fully in said application.

It has also been observed that the presence of an alkyldiarylphosphine (for example, propyldiphenylphosphine or ethyldiphenylphosphine) in the rhodium-catalyzed hydroformylation of the alpha-olefin propylene inhibits catalyst productivity; i.e., the rate at which the desired product aldehydes are formed. Specifically, the addition of small amounts of propyldiphenylphosphine or ethyldiphenylphosphine to rhodium hydroformylation solutions markedly reduced the rate of production of butyraldehydes from propylene, compared to the rate obtained in the absence of the alkyldiarylphosphines.

Although the presence of alkyldiarylphosphines in rhodium-catalyzed hydroformylation processes reduces the catalyst productivity, the stability of such rhodium complex catalysts can be enhanced by providing an alkyldiarylphosphine in the reaction medium and copending, commonly assigned U.S. application Ser. No. 762,335 filed Jan. 25, 1977, abandoned in favor of continuation U.S. application 140,380 filed Apr. 16, 1980 (Belgium Patent 863,267), the entire disclosure of which is incorporated herein by reference thereto, teaches that the reaction conditions can be adjusted to be more severe in order to regain this apparent loss of catalyst productivity while retaining the enhanced catalyst stability.

Said Ser. No. 762,335 further teaches that when a triarylphosphine ligand is employed in the hydroformylation of an alpha-olefin, some alkyldiarylphosphine is produced in situ, the "alkyl" group thereof being derived from the alpha-olefin undergoing hydroformylation and the "aryl" groups thereof being the same as the aryl of the triarylphosphine.

Said Ser. No. 762,335 further discloses that when an alkyldiarylphosphine ligand is present in a liquid reaction medium containing a rhodium complex catalyst consisting essentially of rhodium complexed with carbon monoxide and a triarylphosphine ligand, the resulting rhodium complex catalyst consists essentially of rhodium complexed with carbon monoxide and either one or both of the triarylphosphine ligand and the alkyldiarylphosphine ligand and that the terminology "consists essentially of" is not meant to exclude, but rather to include, hydrogen complexed with the rhodium, in addition to carbon monoxide and triarylphosphine and/or alkyldiarylphosphine. However, this language is meant to exclude other materials in amounts which poison or deactivate the catalyst. Said Ser. No. 762,335 goes on to disclose that particularly advantageous results are achieved when the amount of total free phosphine ligand in the liquid reaction medium is at least about 100 moles per mole of catalytically-active rhodium metal present in the rhodium complex catalyst.

Thus it is known that, despite the obvious advantages of the above inventions, during use the rhodium complex catalyst loses activity (i.e. becomes partially deactivated) and eventually, after prolonged use, the activity of the catalyst will have decreased to such a point that it is no longer economically desirable to operate the hydroformylation process and the catalyst will have to be discharged and replaced with fresh catalyst. Accordingly, due to the high cost of rhodium values the reactivation of such partially deactivated catalysts and/or recovery of the rhodium values of such catalysts is of extreme importance to the state of the art.

SUMMARY OF THE INVENTION

It has now been discovered that rhodium complex concentrates, derived from spent hydroformylation reaction mediums containing partially deactivated rhodium complex catalysts, contain reactivated rhodium and that said concentrates can be employed as catalytic precursors in a hydroformylation process to achieve a substantial increased rate of reaction above that obtained when employing said partially deactivated catalysts. The subject invention represents a substantial advancement in the art in that unlike prior art procedures the use of chemical compounds such as acids are not required for reactivation of the rhodium of the partially deactivated catalyst, nor is it necessary to recover the rhodium metal per se before it can be reused.

Thus, it is an object of this invention to provide a hydroformylation medium which comprises reactivated rhodium complex and triarylphosphine, as well as a method for preparing same, said rhodium complex having been derived from a rhodium complex concentrate prepared from a spent hydroformylation reaction medium. It is another object of this invention to provide an improved process for preparing aldehydes by hydroformylating an olefin in the presence of a rhodium complex catalyst and triarylphosphine, the improvement which comprises employing as a source of rhodium for said catalyst a rhodium complex concentrate prepared from a spent hydroformylation reaction medium. Other objects and advantages from this invention will become readily apparent from the following description and appended claims.

Accordingly a generic aspect of this invention can be described as a process for preparing a hydroformylation medium, containing a rhodium complex and triarylphosphine, which comprises mixing a rhodium complex concentrate with a sufficient amount of triarylphosphine so that there is at least about 10 moles of free triarylphosphine per mole of rhodium present in said medium, said rhodium complex concentrate having been produced by a process which comprises concentrating a spent hydroformylation reaction medium that contains a partially deactivated rhodium complex catalyst and free triarylphosphine, into at least two separate material streams by means of distillation at temperatures of about 20° to about 350° C. and at pressures of about 1000 to about $1 \times 10^{-6}$ mm Hg., wherein one stream is said rhodium complex concentrate (i.e. the distillation residue) containing a major amount of the rhodium of said catalyst and which has been concentrated to about 0.1 to about 30 percent by weight of said spent hydroformylation reaction medium, and the other material stream or streams consist essentially of one or more of the distilled volatile components of said spent hydroformylation reaction medium.

Preferably the above process for preparing said hydroformylation medium also involves employing a sufficient amount of a solvent for said concentrate so that the amount of rhodium present in said liquid hydroformylation medium ranges from about 25 to about 1000 ppm of rhodium calculated as the free metal.

Another generic aspect of this invention can be described as a hydroformylation medium comprising a rhodium complex and at least about 10 moles of free triarylphosphine per mole of rhodium present in said medium, said medium also preferably containing a solvent for said complex such that the amount of rhodium present in said medium ranges from about 25 to about 1000 ppm of rhodium calculated as free metal, and wherein said rhodium complex has been derived from a rhodium complex concentrate which has been produced by a process which comprises concentrating a spent liquid hydroformylation reaction medium that contains a partially deactivated rhodium complex catalyst and free triarylphosphine, into at least two separate material streams by means of distillation at temperatures of about 20° to about 350° C. and at pressures of about 1000 to about $1 \times 10^{-6}$ mm Hg., wherein one stream is said rhodium complex concentrate (i.e. the distillation residue) containing a major amount of the rhodium of said catalyst and which has been concentrated to about 0.1 to about 30 percent by weight of said spent hydroformylation reaction medium, and the other material stream or streams consist essentially of one or more of the distilled volatile components of said spent hydroformylation reaction medium.

Still a further generic aspect of this invention can be described as an improved process for producing aldehydes by hydroformylation of an olefin with hydrogen and carbon monoxide in the presence of a hydroformylation reaction medium comprising a soluble rhodium complex catalyst and at least 10 moles of free triarylphosphine per mole of catalytically active rhodium, the improvement comprising employing as a source of rhodium for said catalyst, a rhodium complex concentrate having been produced by a process which comprises concentrating a spent liquid hydroformylation reaction medium containing a partially deactivated rhodium complex catalyst and triarylphosphine into at least two separate material streams by means of distillation at temperatures of about 20° to about 350° C. and at pressures of about 1000 to about $1 \times 10^{-6}$ mm Hg., wherein one stream is said rhodium complex concentrate (i.e. the distillation residue) containing a major amount of the rhodium of said catalyst and which has been concentrated to about 0.1 to about 30 percent by weight of said spent hydroformylation reaction medium, and the other material stream or streams consist essentially of one or more of the distilled volatile components of said spent liquid hydroformylation reaction medium.

DESCRIPTION OF THE PREFERRED EMBODIMENTS

As seen discussed above one of the basic points of novelty of this invention rests in the discovery that spent hydroformylation reaction mediums containing a partially deactivated rhodium complex catalyst and free triarylphosphine can be reactivated or regenerated by concentrating said mediums into a rhodium complex concentrate by means of distillation. The term "spent hydroformylation reaction medium" as employed herein means a hydroformylation reaction medium, or any part thereof, containing a rhodium complex catalyst and free triarylphosphine of any process directed to producing aldehydes by hydroformylating an olefin with carbon monoxide and hydrogen in the presence of a rhodium complex catalyst and free triarylphosphine and which process has been operated to the extent that said catalyst has become at least partially deactivated. In general it is preferred to concentrate those spent hydroformylation reaction mediums in which the rhodium complex catalyst has become so deactivated that it is no longer economical to continue the hydroformylation process. However, it is not necessary to await such an event, since the concentration procedure of this invention can be carried out if desired on any such spent hydroformylation medium which contains at least a partially deactivated rhodium complex catalyst, i.e., a catalyst which less active than its original counterpart. The extent of deactivation of the catalyst may be determined at any given time during the hydroformylation reaction, e.g., by comparing the conversion rate to product based on such catalyst to the conversion rate obtained using fresh catalyst.

As pointed out by the above prior art, methods for hydroformylating olefins to produce aldehydes with a rhodium complex catalyst in the presence of free triarylphosphine are well known in the art. Thus it should be clear that the particular hydroformylation process for producing aldehydes from an olefin from which the spent hydroformylation reaction mediums employed in the present invention may be derived, as well as the reaction conditions and ingredients of said hydroformylation process, are not critical features of the present invention, since such served only as a means for furnishing the spent hydroformylation reaction medium employed as the starting material of the concentration procedure of the present invention. In general, however, it is preferred to concentrate spent hydroformylation reaction mediums derived from the operational features taught in U.S. Pat. No. 3,527,809 and U.S. Application Ser. Nos. 762,335 and 776,934, discussed above.

Thus the spent hydroformylation reaction mediums employable in this invention comprise a partially deactivated rhodium complex catalyst and free triarylphosphine and can contain additional ingredients which have either been deliberately employed in the hydroformylation process or formed in situ during said process. Examples of such additional ingredients that can be present include the olefin starting materials and aldehyde products of said process, solvents for the catalyst, such as the high boiling liquid condensation products of said aldehydes, as well as alkyl substituted phosphines, and even phosphine oxides formed in situ as a result of adventitious oxygen.

As seen by the prior art discussed above such hydroformylation reactions are preferably carried out in the presence of a rhodium complex catalyst consisting essentially of rhodium complexed with carbon monoxide and a triarylphosphine ligand, and free triarylphosphine. As the hydroformylation reaction continues alkyl substituted phosphine of the formula

wherein R is an alkyl radical, R' is an alkyl or aryl radical and R" is an aryl radical can be formed in situ, the amount of which continues to form over the period of time that a continuous hydroformylation process is operational and said alkyl substituted phosphine ligand, having a greater affinity for rhodium than triarylphosphine, also ties or binds itself to the rhodium thereby resulting in a rhodium complex catalyst consisting essentially of rhodium complexed with carbon monoxide, triarylphosphine ligand and/or said alkyl substituted phosphine ligand (i.e. either one or both of said triarylphosphine ligand and said alkyl substituted phosphine ligand) in the liquid reaction medium of said hydroformylation process. Such alkyl substituted phosphines may also be present in the spent hydroformylation reaction medium employed in this invention as a result of deliberate addition to the initial hydroformylation, if desired, as taught in U.S. Application Ser. No. 762,335 discussed above.

Thus it is to be understood that while the partially deactivated rhodium complex catalyst present in the spent hydroformylation medium employed herein can be any such catalyst resulting from any hydroformylation reaction that employed a rhodium complex catalyst, the preferred spent hydroformylation reaction medium employed in this invention contains a partially deactivated rhodium complex catalyst consisting essentially of rhodium complexed with carbon monoxide and triarylphosphine ligand. Moreover, it is to be understood that the term "complex" means a coordination compound formed by the union of one or more electronically rich molecules or atoms capable of independent existence with one or more electronically poor molecules or atoms, each of which is also capable of independent existence. Triorganophosphorus ligands whose phosphorus atom has one available or unshared pair of electrons are capable of forming a coordinate bond with rhodium. Furthermore the terminology "consisting essentially of" is not meant to exclude, but rather include, hydrogen complexed with the rhodium in addition to said carbon monoxide and triarylphosphine as well as alkyl-substituted phosphine when present in the reaction medium, said hydrogen and carbon monoxide of course being derived from the hydrogen and carbon monoxide gases which are an integral part of any hydroformylation process. Moreover, it is not intended to limit the present invention by the above explanation of how the rhodium is complexed with said phosphines, since it is sufficient for the purpose of this invention to simply point out that the preferred partially deactivated rhodium catalyst is a complex. The theory to how such ligands complex with the rhodium is given e.g. in U.S. Pat. No. 3,527,809 and U.S. Application Ser. No. 762,335 discussed above.

The second main component present in the spent hydroformylation reaction medium employable in this invention is free triarylphosphine. As pointed out above the preferred hydroformylation reactions are carried out in the presence of free triarylphosphine, that is triarylphosphine which is not complexed with the rhodium atom in the complex catalyst. In general while such hydroformylation reactions may be conducted in the presence of at least 10 moles of free triarylphosphine ligand per mole of catalytically active rhodium present in the rhodium complex catalyst, preferably the reaction takes place in the presence of a much larger amount such as at least 50 moles and more preferably at least 100 moles of free triarylphosphine per mole of catalytically active rhodium. As is well known the upper limit of the amount of free triarylphosphine ligand is not particularly critical and is dictated primarily and only by commercial and economical consideration.

The triarylphosphine, both complexed with rhodium and free, present in the spent hydroformylation reaction medium employed in this invention can of course be any triarylphosphine suitable for use in any hydroformylation reaction such as those triarylphosphines and reactions taught by the prior art discussed above. Illustrative triarylphosphine ligands are triphenylphosphine, trinaphthylphosphine, tritolylphosphine, p-(N, N-dimethylamino)phenyl diphenylphosphine, tris(p-biphenyl)-phosphine, tris(p-methoxyphenyl)phosphine, and the like. Triphenylphosphine is presently the preferred triarylphosphine ligand.

Moreover alkyl substituted phosphines such as encompassed by Formula (I) above, may also be present in the spent hydroformylation reaction mediums employable in this invention. Such alkyl substituted phosphines, which may be deliberately added, if desired, to a hydroformylation reaction, are nomally derived from the particular olefin that is hydroformylated and the particular triarylphosphine employed in said hydroformylation process. For example, the hydroformylation or propylene by the preferred procedure described in U.S. Application Ser. No. 776,934 leads to the in situ formation of propyldiphenylphosphine as well as some detectable butyldiphenylphosphine.

Accordingly, the alkyl radical of said alkyl substituted phosphine may be any alkyl radical having from 2 to 20 carbon atoms and more preferably 2 to 10 carbon atoms. They may be straight or branched-chain and may contain groups or substituents which do not essentially interfere with the course of the process of this invention, such as hydroxyl and alkoxy radicals, and the like. Illustrative of such alkyl radicals include ethyl, propyl, isopropyl, butyl, pentyl, hexyl, heptyl, octyl, decyl, dodecyl, octadecyl, 2-ethyl-hexyl, eicosyl, 3-phenyl-propyl, 3-hydroxypropyl, 4-hydroxyhexyl, 4-hydroxyoctyl, 2-ethoxyethyl, 2-methoxyethyl, 3-ethoxypropyl, and the like. Moreover, since it is generally preferred to hydroformylate alpha-olefins containing 2 to 5 carbon atoms the most preferred alkyl radicals of said alkyl substituted phosphines are ethyl, propyl, butyl and pentyl. Likewise, the aryl radical of said alkyl substituted phosphines may correspond to the aryl group of the triarylphosphine ligand employed in the hydroformylation processes as discussed above, the preferred aryl radical being a phenyl radical derived from triphenylphosphine. Thus the most preferred alkyl substituted phosphines are ethyldiphenylphosphine, propyldiphenylphosphine and butyldiphenylphosphine, especially propyldiphenylphosphine. Note, however, that it is not applicants' intention to be bound by any precise discussion or explanation of how said alkyl substituted phosphines are formed in situ, it being sufficient for the purpose of this invention to simply point out that their in situ formation and presence is possible in the spent liquid hydroformylation reaction mediums employable in this invention.

The various amounts of rhodium complex catalyst, triarylphosphine and said alkyl substituted phosphine that can be present in the spent hydroformylation reaction medium employable in this invention are not critical, since such will merely depend upon the particular spent hydroformylation reaction medium desired to be concentrated. Thus the spent hydroformylation reaction medium employable herein will merely correspond to that medium of any hydroformylation reaction of an olefin containing from 2 to 20 carbon atoms, especially alpha-olefins, that comprises a partially deactivated rhodium complex catalyst and free triarylphosphine. Likewise the amounts of said partially deactivated rhodium complex catalyst, triarylphosphine and alkyl substituted phosphine present in said spent hydroformylation reaction medium will merely correspond to those amounts of the corresponding ingredients initially employed and/or obtained in situ in the reaction medium of the hydroformylation process from which it is desired to produce the rhodium complex concentrate that is employable in this invention. In general, the amount of alkyl substituted phosphine present in the spent hydroformylation reaction medium employable in this invention may range from 0 to about 20 weight percent, and more preferably from about 1 to about 10 percent based on the total weight of said spent medium, while the amount of triarylphosphine ligand present may vary from about 0.5 percent be weight to about 40 percent by weight or higher, based on the total weight of said spent medium. If desired, such phosphine compounds in said spent hydroformylation reaction medium can be removed, via the use of an aqueous maleic acid or maleic annydride solution, as seen discussed more fully in our commonly assigned, U.S. Application, Ser. Nos. 40,913 filed May 21, 1979, now abandoned and 108,279 filed Dec. 28, 1979, the entire disclosures of which are incorporated herein by reference thereto, prior to subjecting said spent medium to the concentration procedure employed in this invention. However, such a prior removal of phosphine is not necessary to achieve the desired results of the present invention described herein. The amount of partially deactivated rhodium complex catalyst present in the spent hydroformylation reaction medium employable in this invention will of course be at least that minimum amount (catalytic amount) which is necessary to continue to catalyze the particular hydroformylation reaction from which the spent medium employable in this invention is derived. Generally, the rhodium concentration in said spent medium may range from about 25 ppm to about 1000 ppm, and more preferably from about 50 ppm to about 400 ppm of rhodium calculated as free metal.

It is of course, also to be understood that since such hydroformylation reactions are normally conducted in the presence of a solvent for the rhodium complex catalyst, that the spent hydroformylation reaction mediums employable in this invention may, and preferably do, also encompass the presence of such solvents for said catalyst in the same amounts that such solvents are employed in the liquid reaction medium of said hydroformylation reactions. Such solvents are well known in the art and encompass those described in U.S. Pat. No. 3,527,809 and more preferably the higher boiling liquid aldehyde condensation products which are described more fully, as are methods for their preparation, in U.S. Application Ser. No. 776,934 and U.S. Pat. No. 4,148,830 as discussed above. Accordingly, the amount of solvent present in the spent hydroformylation reaction medium employable in this invention is not critical to the subject invention and will preferably be those amounts employed and/or maintained in situ in the liquid reaction medium of a hydroformylation reaction. Thus, in general, the amount of solvent when present in said spent medium may range from about 10 to about 95 parts be weight based on the total weight of said spent medium.

The spent hydroformylation reaction mediums employable in this invention will also contain at least some portion of the aldehyde products which are being produced by the particular hydroformylation reaction involved from whence said spent mediums are derived. For example, the aldehyde products produced by hydroformylating propylene are butyraldehydes. The amount of such aldehyde products present in said spent mediums will of course merely be dependent upon the particular hydroformylation process involved. In general, such spent mediums may contain from about 0.1 to about 30 percent by weight of such aldehyde products based on the total weight of the spent medium. Of course it is to be further understood that the spent hydroformylation reaction mediums may also contain minor amounts of unreacted olefin starting material and phosphine oxides which correspond to the phosphines present in the hydroformylation process and which oxides are normally formed in situ during said process due to adventitious oxygen.

As pointed out above the rhodium complex concentrate employable in this invention is produced by a process which comprises concentrating a spent hydroformylation reaction medium as defined above into at least two separate material streams by means of distillation at temperatures of about 20° to about 350° C. and at pressures of about 1000 to about $1 \times 10^{-8}$ mm Hg., Hg., wherein one stream is said rhodium complex concentrate (i.e. the distillation residue) containing a major amount of the rhodium of said catalyst and which has been concentrated to about 0.1 to about 30 percent by weight of said spent hydroformylation reaction medium, and the other material stream or streams consist essentially of one or more of the distilled volatiles of said spent hydroformylation reaction medium. More preferably the spent hydroformylation reaction medium is distilled to form a rhodium complex concentrate which has been concentrated to from about 1 to about 10 percent by weight and most preferably to from about 2 to about 6 percent by weight of said spent medium.

The distillation procedure preferably takes place in two stages, the first stage bring conducted at temperatures of about 20° to 250° C., preferably from 20° to 190° C., and pressures of about 1000 to about 0.1 mm Hg., preferably about 150 to 0.5 mm Hg., which may effect up to about a threefold concentration of the spent hydroformylation reaction medium; the second stage of the distillation being conducted at temperatures of about 25° to 350° C., preferably from about 150° to about 300° C., and pressures of about 100 to $1 \times 10^{-6}$ mm Hg., preferably about 20 to 0.1 mm Hg., so as to further concentrate the bottom or residue product of the first stage to the finally desired rhodium complex concentrate which may contain from about 1000 to about 50,000 ppm, more preferably from about 1500 to about 15,000 ppm, and most preferably from about 2,000 to 12,000 ppm, of rhodium calculated as free metal.

The first distillation stage is employed to distill off and remove the most volatile components, e.g. the aldehyde products, that are present in the spent hydroformylation medium since such low boiling volatile components interfere with obtaining the desired low pressures employed in the second distillation stage and needed for the most effective removal of the less volatile (i.e. higher boiling) components. Of course it is obvious that the most volatile components (e.g. the aldehyde products) so removed may be recovered from said distillate stream in any conventional manner or discarded as desired.

The second distillation stage involves taking the liquid residue or bottoms of said first distillation stage containing the partially deactivated rhodium complex catalyst and less volatile components, such as the solvent and phosphine ligands, of the spent hydroformylation reaction medium and subjecting it to further distillation at the reduced pressures given above so as to distill off and remove said remaining high boiling volatile materials. The desired rhodium complex concentrate employable in this invention is thus recovered as the distillation residue of said second stage distillation and contains a major amount of the rhodium of said partially deactivated catalyst (i.e. more than 50 percent by weight, preferably more than 90 percent by weight, of the total amount of rhodium of said catalyst). For obvious economic reasons it is most desirable that the rhodium complex concentrate contain essentially (i.e. greater than 97 percent by weight) all of the rhodium of said partially deactivated catalyst.

The distillation of each separation stage can be carried out by using any suitable distillation system and can take place on a continuous and/or discontinuous (batch) basis. However, care should be taken to avoid overheating the rhodium complex. It is also important to maintain a high vacuum in the second distillation stage so that the temperature required for concentration can be minimized. Thus the distillation is preferably carried out at the lowest temperature and shortest residence time required to achieve the desired rhodium concentration. Because the components of the spent hydroformylation reaction mediums which are to be distilled in accordance with this invention can vary, both in terms of their nature and concentrations, as well as from hydroformylation process to hydroformylation process, it is apparent that no specific residence time can be arbitrarily given as either a maximum or minimum in order to practice this invention. Accordingly it is preferred to employ a thin-film evaporator, such as a wiped-film evaporator, since in such systems residence times at elevated temperatures of less than 10 minutes whould be suitable in most instances, and preferably such residence times will be less then about three minutes, whereas in a kettle-type batch distillation the residence time for the second stage of distillation can be hours. However, batch systems are readily suitable for the first stage of distillation, since such is concerned with only removing the most volatile (lower boiling) components of the spent medium and thus the distillation can be carried out at rather mild temperatures and at much higher pressures than those pressures employed in the second distillation stage. In general, it is preferred to carry out both distillation stages in a thin-film evaporator, especially a wiped-film evaporator. Such evaporators are well known in the art and thus need not be further discussed herein.

Of course, it is also to be understood that the procedure of each distillation stage can be carried out more than once, i.e. repeated until the desired amount of volatiles have been removed and/or the desired rhodium concentration obtained. Indeed, because of the short residence time obtainable by use of a thin-film evaporator, it is generally preferred to repeat the initial concentration procedure of the second stage of distillation at least twice, since such has the advantage of allowing the desired rhodium complex concentrate to be built-up in gradual concentration steps.

It should be noted that reactivation of the rhodium of the partially deactivated catalyst present in the spent hydroformylation reaction mediums concentrated herein is not simply the result of distilling catalyst inhibitors from the rhodium catalyst. A fundamental change in the rhodium species present in the partially deactivated catalyst occurs during the concentration procedure employed herein. The rhodium species found in the rhodium complex concentrates produced by the concentration procedure of this invention are different in that they are generally larger in size than those species found in partially deactivated rhodium complex catalysts. Said rhodium complex concentrates so obtained have a dark brownish color and are highly viscous rhodium complex mediums consisting essentially of rhodium and minor amounts of triarylphosphine (generally less than 10 percent by weight based on the total weight of the concentrate), the remainder consisting essentially of highly boiling aldehyde condensation products and phosphine oxides, said condensation products and oxides having been produced in situ during the hydroformylation process from whence the spent hydroformylation reaction medium starting material is obtained.

It has been surprisingly found that the rhodium complex concentrates prepared according to this invention can be employed as a source of reactivated rhodium for the rhodium complex catalyst of any hydroformylation process. Indeed it has been found that the rate of reaction of a rhodium complex catalyst employed in a hydroformylation process which uses such a rhodium complex concentrate as a source of rhodium for the catalyst of said process is greater than that obtained when employing the spent hydroformylation reaction medium containing the partially deactivated catalyst from whence said concentrate was derived.

It has now been further surprisingly found that adding an oxidant such as oxygen and/or an organic peroxide to the rhodium complex concentrates prepared according to this invention can improve the regenerated activity of the concentrate even further and that such oxidant treated concentrates can lead to even further improvements in hydroformylation activity when employed as a source of rhodium for the catalyst of a hydroformylation process above that obtained when employing the spent hydroformylation reaction medium containing the partially deactivated catalyst from whence said concentrate was derived or even when employing the same concentrate that has not been so treated with the oxidant.

It is difficult to ascertain the precise reasons for such an improvement in the regenerated activity of the concentrate due to its contact with the oxidant. However, it is believed that the oxidant, for whatever reason, somehow renders the larger rhodium clusters obtained in preparing the concentrates according to this invention more susceptible to transformation into the smaller catalytic rhodium species that may be found in an efficient hydroformylation process having a high rate of activity. This phenomenon may be readily observed by the change in color of the concentrate during hydroformylation from dark brown into the yellow solution commonly associated with highly active rhodium complex catalysts during such a hydroformylation process.

The oxidant employed in this invention for treatment of the rhodium complex concentrate may be in the form of a gas or liquid and is selected from the class consisting of oxygen and an organic peroxide, that is to say that the oxidant can be oxygen and/or an organic peroxide. While the preferred oxidant is oxygen it is to be understood that oxygen need not be employed in its pure form, but more preferably and conveniently is employed in the form of air or in admixture with an inert gas, such as nitrogen in order to minimize any explosive hazards. Indeed while oxygen in the form of air is the most preferred and convenient oxidant it too may be diluted with an inert gas such as nitrogen in order to reduce its oxygen content if operating conditions warrant such safety precautions. The liquid organic peroxides which may also be employed as oxidants herein encompass organic peroxides of the formula R—O—O—R', wherein R represents a radical selected from the group consisting of monovalent hydrocarbon radicals of 2 to 20 carbon atoms, carboxylic acyl radicals of 2 to 20 carbon atoms, aroyl radicals of 7 to 20 carbon atoms, alkoxycarbonyl radicals of 2 to 20 carbon atoms and cycloalkoxycarbonyl radicals of 4 to 20 carbon atoms, and wherein R' represents a radical selected from the group consisting of hydrogen and a radical represented by R as defined above. Preferred monovalent hydrocarbon radicals represented by R and R' above are alkyl and aralkyl radicals, especially t-alkyl radicals of 4 to 20 carbon atoms and aralkyl radicals of 8 to 15 carbon atoms. Most preferably R' represents hydrogen (i.e. —H). Illustrative organic peroxides include t-butylhydroperoxide, t-amylhydroperoxide, cumenehydroperoxide, ethylbenzenehydroperoxide, and the like. Such organic peroxides and/or methods for their preparation are well known in the art, the most preferred organic peroxide being t-butylhydroperoxide.

Further it is to be appreciated that the improvement in regenerated activity of the rhodium complex concentrate due to its treatment with the oxidant may be accomplished by adding the oxidant to the concentrate in any manner which seems most convenient and suitable. Thus the method of treating the concentrate with the oxidant is not critical and can be accomplished simply by adding a sufficient amount of oxidant to the concentrate to obtain the desired improvement in the regenerated activity of the concentrate. For instance, the gaseous or liquid oxidant can be added by carrying out the concentration of the spent hydroforylation medium in the presence of the oxidant, or during or after the concentrate is being collected. By way of example the liquid organic peroxides may be added to spent hydroformulation medium prior to the concentration procedure or to the concentrate while or after it is being collected. Likewise oxygen, and more preferably air, can be sparged into the concentrate after it has been collected, as it is being collected or while it is still a film on the walls in the thin film evaporator. The concentrate can also be agitated or stirred so as to create a vortex that will draw air from overhead into said concentrate. Alternatively spraying or atomizing the concentrate into air or allowing air to diffuse into the concentrate while or after concentration may also improve the regenerated activity of the concentrate. However because oxygen is the more preferred oxidant and because diffusion of air into the viscous concentrate can be quite slow, in order to obtain the most optimum results it is generally preferred to thoroughly disperse air throughout the concentrate, such as e.g. by directly feeding air into the concentrate after it has been collected or while it is still a film on the walls in a thin film evaporator or by agitating the concentrate and drawing air into it from overhead. Moreover it should be understood that while the oxidant treatment preferably involves directly adding the oxidant to the concentrate, if desired viscous concentrates may be first diluted with an appropriate solvent to facilitate handling prior to said oxidant treatment.

In view of the fact that the oxidant treatment encompassed herein is designed to obtain a desired improvement in the regenerated activity of the rhodium complex concentrate over that obtained in the absence of such an oxidant treatment and because the components of the concentrate can vary both in terms of their nature and concentrations, it is apparent that no specific values can be arbitrarily given to conditions such as the amount and partial pressure (concentration) of oxidant, temperature, and contact time for the oxidant treatment. Such conditions which may vary greatly, are not narrowly critical and obviously need only be at least sufficient to obtain the improvement desired. For instance, the amount of oxidant added obviously need only be at least a sufficient amount necessary to achieve an improvement in the regenerated activity of the rhodium complex concentrate over that obtained in the absence of such an oxidant treatment. Moreover, there appears to be no upper limit on the maximum amount of oxidant that may be employed save for it obviously not being so great as to create a hazardous explosive situation, e.g. by virtue of large concentrations of oxygen, or so great as to be detrimental to the hydroformylation process in which one wishes to employ the rhodium complex concentrate as the source of rhodium for the catalyst thereof, (e.g., excessive amounts of residual peroxide could be harmful to the phosphine ligand of the hydroformylation process). Thus in some cases a small amount of oxidant may be more beneficial, while in other circumstances a large amount of oxidant may prove more desirable. For example, while only a small amount of oxidant may be needed in a given circumstance, it may be more desirable to use a higher concentration, and therefore a larger amount of oxidant, in order to reduce contact time. Accordingly, treatment conditions such as temperature, partial pressure (concentration) and contact time will also vary greatly depending upon among other things, the oxidant and method of treatment involved, and thus any suitable combination of such conditions may be employed herein. For instance, a decrease in any one of such conditions may be compensated for by an increase in one or both of the other conditions, while the opposite correlation is also true. In general the oxidant may be added to the concentrate at liquid temperatures ranging from 0° C. to about 250° C., while temperatures ranging from about ambient temperature to about 175° C. should be suitable in most instances. Moreover, oxygen partial pressures ranging from as little as $10^{-4}$ to 10 atmospheres should be sufficient for most purposes, while the organic peroxides can be conveniently added to the concentrate at atmospheric pressure. Of course it is obvious that the contact time will be directly related to such conditions as temperature and oxidant concentration and may vary from a matter of seconds or minutes to hours. For example, very low oxygen partial pressures and a contact time of only a matter of a few seconds may be needed when treating the concentrate with air while it exists as a thin film on the hot walls of an evaporator during the concentration procedure due to the high temperature employed in such procedures. On the other hand treating a large volume of collected concentrate with moderate oxygen partial pressures ($10^{-3}$ to 1 atmosphere) at room or ambient temperature may require a contact time of several hours or more.

Thus it should be clear that while the selection of the optimum levels of such variables as discussed above are dependent upon one's experience in the utilization of the subject oxidant treatment, only a certain measure of experimentation should be necessary in order to ascertain those conditions which are optimum for a given situation. However, it should also be clear that one of the beneficial factors involved in such an oxidant treatment as employed herein is the wide processing latitute that one has in selecting the proper combination of conditions that will be most useful in obtaining or at least best approaching a particular desired result or need.

Of course it should be again fully understood that when employing the oxidant treatment of this invention one must be careful to avoid those conditions which could lead to the possibility of explosive detonation occurring by virtue of a large concentration of oxygen in a confined space.

Since the ultimate purpose of this invention is to provide a rhodium complex concentrate having a regenerated activity such that which when used as the source of rhodium for the catalyst of a hydroformylation process will furnish said process with a rate of reaction that will approach the activity of fresh rhodium complex catalyst, the more preferred rhodium complex concentrates of this invention will be those which when employed will furnish such a hydroformylation process with a rate of reaction that is at least equal to 50 percent and most preferably at least equal to 70 percent of that rate of reaction which may be obtained when using a fresh rhodium complex catalyst.

As pointed out herein the regenerated activity of a rhodium complex concentrate prepared according to this invention may be determined by measuring the rate of reaction of a rhodium complex catalyst employed in a hydroformylation process which uses the rhodium complex concentrate as the source of rhodium for the catalyst of said process against the activity of a fresh rhodium complex catalyst employed in the same manner. This effect may be easily determined by carrying out the hydroformylation reactions and by continuously monitoring the rate of hydroformylation. The difference in hydroformylation rate (or difference in catalyst activity) may then be observed in a convenient laboratory time frame.

Accordingly the most preferred rhodium complex concentrates of this invention will be those oxidant treated concentrates which when employed as the source of rhodium for a rhodium-triphenylphosphine complex catalyst will provide a hydroformylation process of propylene to butyraldehyde conducted in the presence of said catalyst and free triarylphosphine and at about 100° C. using a gaseous mixture of propylene: carbon monoxide: hydrogen having molar ratio of about 1:1:1 and a total pressure of about 75 p.s.i., with a rate of butyraldehyde production equal to at least 50 percent and more preferably equal to at least 70 percent of that rate of butyraldehyde production obtained for said hydroformylation process under the same conditions when rhodiumdicarbonylacetylacetonate is employed as the source of rhodium for said rhodiumtriphenylphosphine complex catalyst.

Reactivation of the rhodium by the procedure outlined above allows one to employ the rhodium complex concentrate in the same manner as taught in the prior art discussed above for any conventional catalytic precursor, such as rhodium carbonyl triphenylphosphine acetylacetonate, $Rh_2O_3$, $Rh_4(CO)_{12}$, $Rh_6(CO)_{16}$, $Rh(NO_3)_3$, rhodium dicarbonyl acetylacetonate, and the like. Thus the particular manner in which said rhodium complex concentrate is employed as a source of rhodium for the rhodium complex catalyst of a hydroformylation reaction is not critical to this invention.

For instance, the rhodium complex concentrates prepared according to this invention can be employed per se as a catayltic booster to increase the rate of reaction of any conventionally known hydroformylation process directed to producing aldehydes (such as those prior art processes already herein discussed above) that has already been operational to the extent that the rhodium complex catalyst employed therein (be it a conventional preformed catalyst or one derived in situ from a conventional precursor such as taught in the prior art discussed above or even one derived from a rhodium complex concentrate prepared according to this invention) has become at least partially deactivated. The addition of a minor amount of said rhodium complex concentrate to the spent hydroformylation reaction mediums of such hydroformylation processes provides a source of active rhodium for the in situ formation of additional amounts of rhodium complex catalyst, thereby providing the means for an increase in the rate of reaction of said hydroformylation process. The amount of rhodium complex concontrate employed in such a fashion need of course be only that amount necessary to provide an increase in catalytic activity over that being obtained prior to the addition of said concentrate to the spent hydroformylation reaction medium.

Moreover, the rhodium complex concentrates of this invention are especially suitable for employment as the primary source of rhodium for rhodium complex catalysts formed in a hydroformylation process. Preparation of the hydroformylation reaction mediums using said rhodium complex concentrates as the primary catalytic precursor can be carried out in any manner since such is not a critical factor of the present invention. However, it is generally preferred to first prepare a diluted hydroformylation medium of said rhodium complex concentrate and triarylphosphine, which contains rhodium and triarylphosphine in the concentrations normally desired for a hydroformylation process.

Accordingly hydroformylation mediums can be prepared by combining said rhodium complex concentrates with a sufficient amount of triarylphosphine and preferably sufficient solvent for said complex so that said mediums comprise a solubilized rhodium complex and free triarylphosphine, wherein the amount of free triarylphosphine present is at least about 10 moles, preferably at least about 50 moles and more preferably at least about 100 moles, per mole of rhodium present therein, and also preferably wherein the amount of rhodium present in said medium ranges from about 25 to about 100 ppm rhodium and more preferably from about 50 to about 400 ppm to rhodium calculated as free metal.

Such a dilution of the rhodium complex concentrate with triarylphosphine and a solvent to such a hydroformylation medium can be easily carried out merely by mixing the ingredients involved in any suitable manner and in any order. Generally, however, it is preferred to make up a solution of the triarylphosphine and solvent and then add the viscous rhodium complex concentrate to said solution.

Of course, it is obvious that, since the purpose of the hydroformylation medium of this invention is to be employed in a hydroformylation process to produce aldehydes from olefins as discussed above, the triarylphosphines and solvents, as well as the amounts of ingredients involved, which can be used to produce such hydroformylation mediums can correspond to any triarylphosphine, solvent and amounts thereof employable in a hydroformylation processes.

For example obviously the amount of rhodium complex concentrate employed to form said hydroformylation medium need only be that minimum amount which is necessary to provide the desired rhodium concentration of said medium (which concentration as seen above can range from about 25 ppm to about 1000 ppm, preferably from about 50 ppm to about 400 ppm) and which will furnish the basis for at least that catalytic amount of rhodium necessary to catalyze the particular hydroformylation process desired.

Likewise, the triarylphosphine, both complexed with rhodium and free, present in the novel hydroformylation medium of this invention can of course be any triarylphosphine suitable for use in any hydroformylation reaction such as those triarylphosphines and reactions already disclosed above. The preferred triarylphosphine is of course triphenylphosphine. The amount of said triarylphosphine present may vary from about 0.5 percent by weight to 40 percent by weight or higher, based on the total weight of said hydroformylation medium, and as pointed out above is preferably present in that amount sufficient to provide at least 10 moles, preferably at least about 50 moles, and more preferably at least about 100 moles of free triarylphosphine per mole of rhodium present in said hydroformylation medium. Again the upper limit of the amount of free triarylphosphine is not particularly critical and would be dictated largely by commercial and economic considerations.

In the same vein the solvents for the rhodium complex concentrate employed to prepare the novel hydroformylation medium of this invention can of course be any solvent which is also suitable for use in the hydroformylation reaction discussed above. Illustrative solvents encompass those described in U.S. Pat. No. 3,527,809, and more preferably include aldehydes corresponding to the aldehyde products desired to be produced by said hydroformylation reactions (such as n-butyraldehyde) and/or higher boiling liquid aldehyde condensation products corresponding to the high boiling liquid aldehyde condensation product mixtures produced in situ during said hydroformylation reaction such as discussed above (e.g. butyraldehyde trimers). While hydroformylation reactions initially effected in the presence of said aldehyde product solvents will immediately begin forming said higher boiling aldehyde condensation products during the reaction, such condensation products can be preformed if desired, and used accordingly. The amount of such solvents employed of course need only be that amount sufficient to provide the hydroformylation medium (along with the rhodium complex concentrate and triarylphosphine) with the particular rhodium concentration desired for said medium, such as that already disclosed above, and which will furnish the basis for at least that catalytic amount of rhodium necessary to catalyze the particular hydroformylation process desired. In general the amounts of solvent may range from as little as about 5 percent be weight up to about 95 percent by weight or more based on the total weight of the hydroformylation medium.

It has further been surprisingly found that washing the above discussed novel reactivated hydroformylation mediums of this invention prior to their use in a hydroformylation process, with water or more preferably an aqueous alkaline solution, can lead to an even further increase in the rate of hydroformylation activity above that obtained using such reactivated hydroformylation mediums that have not been so washed. It is to be noted that such a washing procedure, unlike that in U.S. Pat. No. 3,555,098, is not being used herein for the purpose of extracting retarding acids that may accumulate in a hydroformylation process. For some reason unknown at the present time, such a washing procedure as employed herein, apparently increases the rate of conversion of at least some of the larger rhodium species present in the regenerated rhodium complex concentrate into more catalytically active smaller rhodium species thereby increasing the rate of hydroformylation compared to that obtained when said washing procedure has not been employed.

Accordingly, it is generally preferred to wash said novel hydroformylation mediums with water or more preferably with an aqueous alkaline solution prior to using same in a hydroformylation reaction. Said washing procedure merely comprises washing the resultant novel hydroformylation medium with water or an aqueous alkaline solution; allowing the resultant mixture to settle into two distinct liquid phases; and separating the aqueous phase from the non-aqueous washed hydroformylation medium phase.

Suitable alkaline materials for the aqueous alkaline solution include e.g. the alkali metal, alkaline earth metal and ammonium hydroxides and carbonates, such as sodium bicarbonate, sodium carbonate, sodium hydroxide, potassium hydroxide, lithium hydroxide, cesium hydroxide, barium hydroxide, calcium hydroxide, ammonium hydroxide, and the like. The concentration of the alkaline material in the aqueous wash can be varied up to the limit of the solubility of the particular alkaline material employed. Preferably the alkaline material is employed as aqueous solutions containing from about 0.1 to about 10 weight percent of the alkaline material. The more preferred aqueous alkaline solutions are about 5 to 10 percent by weight solutions of sodium bicarbonate.

The washing is effected by simply mixing the aqueous alkaline solution with the hydroformylation medium to be treated. The washing may be conducted in air or under nitrogen, at atmospheric pressure or elevated pressures and at temperatures of from 25° C. to about 100° C. Preferably the washing is done at atmospheric pressure and at a temperature of about 25° to 65° C. The washing is normally completed within a matter of minutes, e.g. 1 to 10 minutes. The amount of washing medium employed is not narrowly critical and may range from about 0.1 to about 1 parts by volume per part of hydroformylation medium treated. In general it is most preferred to wash the hydroformylation medium with about 0.1 to 0.5 parts by volume of about a 5 weight percent aqueous sodium bicarbonate solution. Moreover, if desired, and such is normally preferred, after the hydroformylation medium has been washed with the aqueous alkaline solution and the aqueous alkaline solution removed, the hydroformylation medium can then be further washed one or more times with water to insure removal of any excess amount of the base compound employed in the initial alkaline wash. Of course, it is obvious that the water employed in such subsequent washings must also be separated from the hydroformylation medium prior to its use in a hydroformylation process and that such can also be accomplished by simple phase separation as described above.

Further as pointed out above the present invention also provides an improved process for producing aldehydes by hydroformylation of an olefin with hydrogen and carbon monoxide in the presence of a soluble rhodium complex catalyst and at least 10 moles of free triarylphosphine per mole of catalytically active rhodium, the improvement which comprises employing as a source of rhodium for said catalyst, a rhodium complex concentrate having been produced from a spent hydroformylation reaction medium in the manner already herein discribed above.

The particular hydroformylation reactions encompassed by this invention, which can employ said rhodium complex concentrates in any manner desired, such as already herein disclosed above, as a source of rhodium for the rhodium complex catalyst, as well as the reaction conditions of such hydroformylation reactions are not critical features of this invention and such are well known as seen already herein discussed above. The preferred hydroformylation processes are taught in U.S. Pat. No. 3,527,809, and U.S. Applications Ser. Nos. 762,335 and 776,934.

Such hydroformylation processes involve producing aldehydes, preferably rich in their normal isomers, by reacting an olefin with hydrogen and carbon monoxide gas in a liquid reaction medium which contains a soluble rhodium complex catalyst and at least 10 moles of free triarylphosphine per mole of catalytically active rhodium and wherein the reaction conditions consist essentially of (1) a temperature in the range of from about 50° C. to 145° C., preferably from about 90° C. to about 120° C.; (2) a total gas pressure of hydrogen, carbon monoxide and olefin of less than about 1500 psia., preferably less than about 400 psia and more preferably less than about 350 psia.; (3) a carbon monoxide partial pressure of less than about 100 psia., preferably from about 1 to about 50 psia.; and (4) a hydrogen partial pressure of less than about 400 psia., preferably from about 20 to about 200 psia. Moreover, it is generally preferred that the amount of free triarylphosphine present is at least about 50 moles, and more preferably at least about 100 moles per mole of catalytically active rhodium.

The olefins that may be hydroformylated by the process of this invention are well known in the art and may contain from 2 to 20 carbon atoms. In general it is preferred to hydroformylate alpha-olefins having from 2 to 20 carbon atoms and more preferably alpha-olefins having from 2 to 6 carbon atoms, such as ethylene, propylene, 1-butylene, 1-pentylene, 1-hexylene, and the like. Said olefins used in the process of this invention may be straight-chained or branched-chain and may contain groups or substituents which do not essentially interfere with the course of the hydroformylation reaction such as generically taught in the above discussed prior art, especially U.S. Pat. No. 3,527,809. The process of the present invention is especially useful for the hydroformylation of propylene to form butyraldehydes having a high normal to iso ratio.

The triarylphosphines which may be employed in the hydroformylation process of this invention are also well known as seen by the above discussed prior art and illustrative examples of such triarylphosphines are set forth above. The most preferred triarylphosphine is triphenylphosphine.

The rhodium complex catalyst of the hydroformylation processes of this invention includes any rhodium complex catalyst which employs as a source of rhodium for said catalyst, a rhodium complex concentrate having been produced from a spent hydroformylation reaction medium as described herein. Methods of employing said rhodium complex concentrates as the source of rhodium for said catalysts have already been described herein above. As taught in the prior art discussed above the active rhodium complex catalyst is generally formed in the reaction medium under the conditions of hydroformylation although it is also possible to perform such active catalysts from the rhodium complex concentrates employed in this invention. Accordingly, as in the case of the prior art discussed above the rhodium complex catalysts may be described as consisting essentially of carbon monoxide and triarylphosphine. Of course, as already explained above the terminology "consisting essentially of" in said catalyst definition is not meant to exclude, but rather include hydrogen complexed with the rhodium, as well as, alkyl substituted phosphines complexed with the rhodium when present in the reaction medium as a result of deliberate addition or in situ formation.

It is also preferred to effect the hydroformylation reaction of this invention in a liquid phase in the reaction zone which contains the rhodium complex catalyst and, as a solvent therefore, the higher boiling liquid aldehyde condensation products, such as already herein discussed above and taught in the above mentioned prior art.

It is also generally preferred to carry out the hydroformylation process of this invention in a continuous manner and particularly according to the continuous process that employs the gas recycle technique described in above discussed U.S. Applications, Ser. Nos. 762,335 and 776,934. Said gas recycle involves supplying to the liquid reaction medium a gaseous recycle stream containing at least hydrogen and unreacted olefin, and also supplying make-up quantities of carbon monoxide, hydrogen and olefin to said liquid reaction medium while removing from said liquid reaction medium a vapor phase mixture comprising unreacted olefin, hydrogen, vaporized aldehyde products and vaporized high boiling condensation products of said aldehydes, recovering said aldehyde and said aldehyde condensation products from said vapor phase mixture and forming said gaseous recycle steam, wherein the vaporized aldehyde condensation products are prepreferably removed from said liquid reaction medium in said vapor phase mixute at a rate which is substantially equal to the rate of their formation in said liquid reaction medium whereby the size of said liquid reaction medium is maintained substantially constant.

Of course, it is to be understood that the hydroformylation process of this invention can be carried out in the presence of additional materials, that are deliberately added to the hydroformylation reaction medium, if desired, for specific purposes or formed in situ during the hydroformylation process such as alkyl substituted phosphines, and the like which have already been discussed above and are known in the art.

Moreover it should be apparent that the amounts of the various individual components employed in the hydroformylation process of this invention are not narrowly critical to the operation of the present invention and that such general and preferred amounts have already been herein discussed above and can be readily found in the above described prior art.

Finally, the aldehyde products of the hydroformylation process this invention have a wide range of utility that is well known and documented in the prior art e.g. they are especially useful as starting materials for the production of alcohols.

The following examples are illustrative of the present invention and are not to be regarded as limitative. It is to be understood that all of the parts, percentages and proportions referred to herein and in the appended claims are by weight unless otherwise indicated.

EXAMPLE 1

An externally heated twelve liter distillation flask equipped with a goose-neck condenser and connected to a vacuum pump was used to batch distill about 8736 grams of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 30 percent of that of fresh catalyst. After charging said spent reaction medium to the flask the pressure in the flask was gradually reduced to about 100 mm Hg. Heat was then applied to distill said spent reaction medium at temperatures of about 24° C. to about 153° C., while the pressure was further reduced to about 0.5 mm Hg. during the distillation. After seven hours about 4373 grams of distillate (low-boilers) consisting mainly of butyraldehyde and essentially no rhodium had been collected. The residue in the flask consisted of about 4293 grams of the higher boiling components of said distilled spent reaction medium and contained essentially all of the rhodium of said catalyst.

A sample of the distillation residue of said above described batch distillation was further concentrated by distillation in a glass wiped-film evaporator which was heated to about 230°–237° C. with an electrical heating tape and which was operated at about 0.4–0.5 mm Hg.. An essentially rhodium free distillate of said sample feed was collected overhead. A highly viscous rhodium complex concentrate distillation residue was obtained from the bottom of the wiped-film evaporator at a rate of 19.8 grams per hour which was found to contain about 5749 ppm rhodium, which represents essentially all of the rhodium (about 99.4%) contained in the feed sample and about 7.5 weight percent of triphenylphosphine, the remainder consisting essentially of triphenylphosphine oxide and higher boiling organic components e.g. aldehyde pentamers.

About 15.6 grams of said rhodium complex concentrate distillation residue obtained from the thin-film evaporator was diluted with about 15 grams of triphenylphosphine and about 260 grams of Texanol ®, a mixture of butyraldehyde trimers, to produce a solution containing about 298 ppm rhodium and 4.6 weight percent triphenylphosphine (about 61 moles of free triphenylphosphine per mole of rhodium). A sample of said solution was then used to catalyze the hydroformylation of propylene in a stirred autoclave reactor at about 100° C. under about 75 psi. of carbon monoxide, hydrogen and propylene in a 1:1:1 mole ratio. The activity of the rhodium complex catalyst of said process which employed said concentrate as its source of rhodium was found to be about 52 percent as compared to the activity of fresh rhodium complex catalyst under the same conditions.

Another sample of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 81 percent as compared to the activity of fresh rhodium complex catalyst under the same conditions.

EXAMPLE 2

About a 4450 gram sample of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 30 percent of that of fresh catalyst was distilled in a glass wiped-film evaporator which had been heated to about 160°–175° C. with an electrical heating tape while the pressure was maintained at about 7–10 mm Hg. An essentially rhodium free distillate consisting essentially of butyraldehyde and other low boiling components was collected at a rate of 128 grams per hour. In addition a total of about 3567 grams of a distillation residue consisting of the higher boiling components of the distilled spent medium and essentially all of the rhodium of the feed sample was collected at the bottom of the evaporator at a rate of about 526 grams per hour.

Said distillation residue obtained as described above was further concentrated by reintroducing the residue for a second pass through the evaporator which had been heated to about 233°–242° C. and which was operated at about 0.5–1.2 mm Hg.. An essentially rhodium free distillate of said sample feed was collected overhead. In addition a highly viscous rhodium complex concentrate distillation residue was obtained from the bottom of the wiped-film evaporator which was found to contain about 13,227 ppm rhodium, which represents more than 99.9% of the rhodium contained in the residue feed, and less than 5 percent of triphenylphosphine, the remainder consisting essentially of triphenylphosphine oxide and higher boiling organic components e.g. aldehyde pentamers.

A sample of said rhodium complex concentrate distillation residue containing about 13,227 ppm rhodium was diluted with sufficient triphenylphosphine and sufficient Texanol ®, to produce a solution containing about 328 ppm rhodium and about 5 weight percent triphenylphosphine (about 60 moles of free triphenylphosphine per mole of rhodium). A sample of said solution was then used to catalyze the hydroformylation of propylene in a stirred autoclave reactor at about 100° C. under about 75 psig of carbon monoxide, hydrogen and propylene in a 1:1:1 mole ration. The activity of the rhodium complex catalyst of said process which employed said concentrate as its source of rhodium was found to be about 57 percent as compared to the activity of fresh rhodium complex catalyst under the same conditions.

Another sample of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 85 percent as compared to the activity of fresh rhodium complex catalyst under the same conditions.

EXAMPLE 3

By way of comparison of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 30 percent of that of fresh catalyst, was batch distilled at about 100° C. and about 10 mm Hg. to remove mainly only the butyraldehyde products and lower boiling components of the medium.

A sample of the distillation residue obtained from the above distillation process was then used to catalyze the hydroformylation of propylene in a stirred autoclave reactor at about 100° C. under about 75 psi. of carbon monoxide, hydrogen, and propylene in a 1:1:1 mole ratio. The activity of the rhodium complex catalyst of said process was found to be about 29 percent as compared to the activity of fresh rhodium complex catalyst under the same conditions.

Another sample of said distillation residue so obtained as described above was first washed with a 5 weight percent aqueous solution of sodium bicarbonate and then with water and dried prior to being used in hydroformylating propylene under the same conditions as described above. In this instance the activity of the rhodium complex catalyst was found to remain about the same, that is about 34 percent as compared to the activity of fresh rhodium complex catalyst under the same conditions.

EXAMPLE 4

About 4224 grams of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 23 percent of that of fresh catalyst was charged to a 5 liter glass distillation vessel equipped with a twenty tray column and distilled at about 25 to about 185° C. and at about 0.7 to 50 mm Hg. The essentially rhodium free distillate consisted essentially of mixed butyraldehydes and other low boiling components.

About 85 grams of the residue of said above distillation was then charged to a high vacuum distillation apparatus equipped with a three stage oil diffusion pump and a mechaical vacuum pump. The mechanical pump was engaged and the pressure was reduced to about $5 \times 10^{-2}$ mm Hg. Then the diffusion pump was engaged and the pressure was further reduced to about $5 \times 10^{-5}$ to $6 \times 10^{-5}$ mm Hg. Heat was then applied with an electrical heating tape and distillation began at about 50° C. The temperature of the distillation was gradually increased to about 93° C. The essentially rhodium free distillate, so removed, consisted essentially of butyraldehyde trimers, other high boiling butyraldehyde condensation products and triphenylphosphine. In addition a rhodium complex concentrate residue was obtained which was found to contain about 2208 ppm rhodium, which represents more than 97 percent of the rhodium in the spent medium feed, and a minor amount (about 0.2 area percent by gas chromatography analysis) of triphenylphosphine, the remainder consisting essentially of triphenylphosphine oxide and higher boiling organic components, e.g. aldehyde pentamers.

A sample of said rhodium complex concentrate residue so obtained was diluted with sufficient triphenylphosphine and Texanol ® to produce about a 50 ml. hydroformylation solution containing about 303 ppm rhodium and about 5.3 weight percent triphenylphosphine (about 69 moles of free triphenylphosphine per mole of rhodium). A sample of said solution was then used to catalyze the hydroformylation of propylene in a stirred autoclave reactor at about 100° C. under about 75 psi. of carbon monoxide, hydrogen and propylene in a 1:1:1 mole ratio. The activity of the rhodium complex catalyst of said process which employed said concentrate as its source of rhodium was found to be about 39 percent as compared to the activity of fresh rhodium complex catalyst under the same conditions.

Another sample of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 71 percent as compared to the activity of fresh rhodium complex catalyst under the same conditions.

EXAMPLE 5

About a 169 gram sample of the essentially butyraldehyde free residue obtained from the initial distillation stage (25° to 185° C.; 0.7 to 50 mm Hg.) of Example 4 above was charged to a vacuum distillation apparatus equipped with a three stage oil diffusion pump and a mechanical vacuum pump. The distillation was conducted at about 100° C. and at about $5 \times 10^{-5}$ mm Hg. About 147 grams of a distillate consisting essentially of about 36 ppm rhodium, butyraldehyde trimers, other high boiling butyraldehyde condensation products and triphenylphosphine was obtained. In addition about 15 grams of a highly viscous rhodium complex concentrate residue was also obtained which was found to contain about 3362 ppm rhodium and a minor amount of triphenylphosphine, the remainder consisting essentially of triphenylphosphine oxide and higher boiling organic components, e.g. aldehyde pentamers.

A sample of said rhodium complex concentrate residue so obtained was diluted with sufficient triphenylphosphine and Texanol ® to produce about a 50 ml. hydroformylation solution containing about 306 ppm rhodium and about 5.0 weight percent triphenylphosphine (about 64 moles of free triphenylphosphine per mole of rhodium). A sample of said solution was then used to catalyze the hydroformylation of propylene in a stirred autoclave reactor at about 100° C. under about 75 psi. of carbon monoxide, hydrogen and propylene in a 1:1:1 mole ratio. The activity of the rhodium complex catalyst of said process which employed said concentrate as its source of rhodium was found to be about 49 percent as compared to the activity of fresh rhodium complex catalyst under the same conditions.

Another sample of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 77 percent as compared to the activity of fresh rhodium complex catalyst under the same conditions.

EXAMPLE 6

A sample of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose activity had declined to about 30 percent of that of fresh catalyst was charged to a roto evaporator and distilled under reduced pressure and at an elevated temperature so as to remove essentially only the butyraldehydes and other low boiling aldehyde condensation products from said medium as the distillate. About 190 grams of the essentially butyraldehyde-free residue obtained from said above distillation was then charged to a high vacuum distillation apparatus equipped with a three stage oil diffusion pump and a mechanical vaccuum pump. The last traces of butyraldehydes were removed at ambient temperature and reduced pressures. Then the pressure was reduced further to about $2.5 \times 10^{-2}$ mm Hg. The diffusion pump was engaged and the still temperature was gradually increased to 100° C. at about $6 \times 10^{-5}$ mm Hg. After about 48 hours, the distillation was stopped. The distillate, so removed, was found to consist essentially of about 7 ppm rhodium, butyraldehyde trimers, other high boiling aldehyde condensation products and triphenylphosphine. In addition a highly viscous rhodium complex concentrate residue was obtained which was found to contain about 4766 ppm rhodium and a minor amount of triphenylphosphine, the remainder consisting essentially of triphenylphosphine oxide and higher boiling organic components, e.g. aldehyde pentamers. A sample of said rhodium complex concentrate residue so obtained was diluted with sufficient triphenylphosphine and Texanol® to produce about a 50 ml. hydroformylation solution containing about 299 ppm rhodium and about 5.2 weight percent triphenylphosphine (about 68 moles of free triphenylphosphine per mole of rhodium). A sample of said solution was then used to catalyze the hydroformylation of propylene in a stirred autoclave reactor at about 100° C. under about 75 psi. of carbon monoxide, hydrogen and propylene in a 1:1:1 mole ratio. The activity of the rhodium complex catalyst of said process which employed said concentrate as its source of rhodium was found to be about 71 percent as compared to the activity of fresh rhodium complex catalyst under the same conditions.

Another sample of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 87 percent as compared to the activity of fresh rhodium complex catalyst under the same conditions.

EXAMPLE 7

About 865 pounds of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 30 percent of that of fresh catalyst, was fed to a standard wiped-film evaporator at feed rates ranging from about 135 to about 322.5 pounds per hour and distilled in said evaporator which had been heated with oil at temperatures ranging from about 207° to about 243° C. and under pressures ranging from about 100 to about 150 mm Hg. The distillate collected overhead consisted essentially of mixed butyraldehyde products and other low boiling aldehyde condensation products, while the distillation residue so obtained contained practically all of the rhodium and triphenylphosphine present in the spent medium feed.

The distillation residue so collected was further concentrated by refeeding said residue to the wiped-film evaporator at feed rates ranging from about 147.5 to about 281.3 pounds per hour, while the evaporator was heated at temperatures ranging from about 232° to about 290° C. and under pressures ranging from about 3.1 to about 6.0 mm Hg. A free-flowing fluid distillate consisting essentially of butyraldehyde trimers, other high boiling aldehyde condensation products and triphenylphosphine was removed overhead. In addition a composite residue was obtained from the evaporator which contained about 912 ppm rhodium and which also consisted essentially of butyraldehyde trimers, other higher boiling aldehyde condensation products, triphenylphosphine and triphenylphosphine oxide. Samples of the individual rhodium complex concentrate residues that made up said composite residue were collected periodically and were found to have concentrations of rhodium ranging from about 1600 to about 2700 ppm rhodium. Higher values of rhodium were found in said samples since the sampling was not initiated until the conditions in the wiped-film evaporator had reached equilibrium.

A portion of one of said individual rhodium complex concentrate samples so obtained containing about 2665 ppm rhodium was diluted with sufficient triphenylphosphine and Texanol® to produce a hydroformylation solution containing about 295 ppm rhodium and about 5.0 weight percent triphenylphosphine (about 67 moles of triphenylphosphine per mole of rhodium). A portion of said solution was then used to catalyze the hydroformylation of propylene in a stirred autoclave reactor at about 100° C. under about 75 psi. of carbon monoxide, hydrogen and propylene in a 1:1:1 mole ratio. The activity of the rhodium complex catalyst of said process which employed said concentrate as its source of rhodium was found to be about 74 percent as compared to the activity of fresh rhodium complex catalyst under the same conditions.

Another portion of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to be about 67 percent as compared to the activity of fresh rhodium complex catalyst under the same conditions.

EXAMPLE 8

The composite residue product containing about 912 ppm rhodium of Example 7 was further concentrated by refeeding said residue to the wiped-film evaporator at feed rates ranging from about 117.5 to about 153.8 pounds per hour while the evaporator was heated at temperatures ranging from about 275° to 279° C. and under pressures ranging from about 2.9 to 3.9 mm Hg. An essentially rhodium free distillate consisting essentially of butyraldehyde trimers, other high aldehyde condensation products and triphenylphosphine was removed overhead. In addition a more concentrated composite residue than that of the feed material was obtained from the evaporator which contained practically all of the rhodium of the feed material and which also consisted essentially of triphenylphosphine oxide and higher boiling aldehyde condensation products (e.g. butyraldehyde pentamers). Samples of the individual rhodium complex concentrate residues that made up said more concentrated composite residue were collected periodically and these samples were found to have concentrations of rhodium ranging from about 6500 to about 11,600 ppm rhodium.

A portion of one of said individual rhodium complex concentrate samples so obtained containing about 6481 ppm rhodium was diluted with sufficient triphenylphosphine and Texanol ® to produce a hydroformylation solution containing about 340 ppm rhodium and about 5.0 weight percent triphenylphosphine (about 58 moles of free triphenylphosphine per mole of rhodium). A portion of said solution was then used to catalyze the hydroformylation of propylene in a stirred autoclave reactor at about 100° C. under about 75 psi. of carbon monoxide, hydrogen and propylene in a 1:1:1 mole ratio. The activity of the rhodium complex catalyst of said process which employed said concentrate as its source of rhodium was found to be about 76 percent as compared to the activity of fresh rhodium complex catalyst under the same conditions.

Another portion of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to be about 80 percent as compared to the activity of fresh rhodium complex catalyst under the same conditions.

EXAMPLE 9

A portion of one of said individual rhodium complex concentrate samples obtained as described in Example 8 above and containing about 11,588 ppm rhodium was diluted with sufficient triphenylphosphine and Texanol ® to produce a hydroformylation solution containing about 326 ppm rhodium and about 5.0 weight percent triphenylphosphine (about 68 moles of free triphenylphosphine per mole of rhodium).

A portion of said solution was then used to catalyze the hydroformylation of propylene in a stirred autoclave reactor at about 100° C. under about 75 psi of carbon monoxide, hydrogen and propylene in a 1:1:1 mole ratio. The activity of the rhodium complex catalyst of said process which employed said concentrate as its source of rhodium was found to be about 67 percent as compared to the activity of fresh rhodium complex catalyst under the same conditions.

Another portion of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 83 percent as compared to the activity of fresh rhodium complex catalyst under the same conditions.

EXAMPLE 10

By way of comparison a sample of the same spent hydroformylation reaction medium initially employed in Example 7 above, was used to catalyze the hydroformylation of propylene in a stirred autoclave reactor at about 100° C. under about 75 psi. of carbon monoxide, hydrogen and propylene in a 1:1:1 mole ratio. The activity of the rhodium complex catalyst of said process was found to be about 30 percent as compared to the activity of fresh rhodium complex catalyst under the same conditions.

Another sample of said spent hydroformylation reaction medium was first washed with a 5 weight percent aqueous solution of sodium bicarbonate and then with water and dried prior to being used to hydroformylate propylene under the same conditions as described above. In this instance the activity of the rhodium complex catalyst was found to be about 40 percent as compared to the activity of fresh rhodium complex catalyst under the same conditions.

EXAMPLE 11

A 17.3 gram sample of the same individual rhodium complex concentrate sample obtained as described in Example 8 above and containing about 11,588 ppm rhodium, was mixed with about 120 grams of triphenylphosphine and about 862.7 grams of Texanol ® to produce a hydroformylation solution containing about 211 ppm rhodium and about 12.3 percent triphenylphosphine (about 236 moles of free triphenylphospnine per mole of rhodium). Said hydroformylation so prepared was then washed with a 5 weight percent aqueous solution of sodium bicarbonate and then with water and dried.

About an 800 ml. portion of said hydroformylation solution, washed as described above, was then charged to a continuous gas recycle reactor and used in the hydroformylation of propylene with carbon monoxide and hydrogen at about 105° C. and about 230 psi. of total gas pressure in the reactor. After one day of operation the activity of the rhodium complex catalyst of said hydroformylation was found to be about 71 percent as compared to the activity of fresh rhodium complex catalyst after one day under the same conditions. After 7 days of operation the activity of the rhodium complex catalyst of said hydroformylation was found to be about 87 percent as compared to the activity of fresh rhodium complex catalyst after 7 days under the same conditions. After 17 days of operation the activity of the rhodium complex catalyst of said hydroformylation was found to be about 85 percent as compared to the activity of fresh rhodium complex catalyst after 17 days under the same conditions.

EXAMPLE 12

A 3.5 gram sample of the same individual rhodium complex concentrate sample, obtained as described in Example 8 above and containing about 11,588 ppm rhodium was mixed with about 24 grams of triphenylphosphine and about 172.5 grams of Texanol ® to produce a hydroformylation solution containing about 200 ppm rhodium and about 12 weight percent triphenylphosphine (about 236 moles of free triphenylphosphine per mole of rhodium).

About a 20 ml. portion of said hydroformylation solution was then charged to a continuous single-pass reactor and used in the hydroformylation of propylene with carbon monoxide and hydrogen at about 105° C. and about 165 psi. of total gas pressure in the reactor. After one day of operation the activity of the rhodium complex catalyst of said hydroformylation was found to be about 88 percent as compared to the activity of fresh rhodium complex catalyst after 1 day under the same conditions. After 23 days of operation the activity of the rhodium complex catalyst of said hydroformylation was found to be essentially the same as compared to the activity of fresh rhodium complex catalyst after 23 days under the same conditions.

Another sample of said hydroformylation solution so prepared as described above was first washed with a 5 weight percent aqueous solution of sodium bicarbonate and then with water and dried prior to being used in the hydroformylation of propylene under the same conditions as described above. After 1 day of operation the rhodium complex catalyst of said hydroformylation was found to have an activity of about 87 percent compared to the activity of fresh rhodium complex catalyst after 1 day under the same conditions. After 23 days of operation the rhodium complex catalyst of said hydroformylation was found to be essentially the same as compared to the activity of fresh rhodium complex catalyst after 23 days under the same conditions.

EXAMPLE 13

A portion of one of said individual rhodium complex concentrate samples obtained as described in Example 7 above, and containing about 2419 ppm rhodium, was diluted with sufficient triphenylphosphine and Texanol® to produce a hydroformylation solution containing about 230 ppm rhodium and about 5.0 weight percent triphenylphosphine (about 85 moles of triphenylphosphine per mole of rhodium).

A series of individual samples of said hydroformylation solution were then washed with water or 5 weight percent solutions of various base materials followed by a water wash to insure removal of the base material employed. Each washed solution was dried and then used to catalyze the hydroformylation of propylene in a stirred autoclave reactor at about 100° C. under about 75 psi. of carbon monoxide, hydrogen and propylene in a 1:1:1 mole ratio. The relative activity of each sample solution, prior to washing and after washing, is given in TABLE I below, as compared to the arbitrary relative activity value of 1.00 assigned to said sample solution prior to washing.

TABLE I

| Sample No. | Washing Agent | pH | Relative Activity |
|---|---|---|---|
| 1 | None | — | 1.00 |
| 2 | H$_2$O | 7.7 | 1.09 |
| 3 | NaHCO$_3$ | 9.0 | 1.15 |
| 4 | Na$_2$CO$_3$ | 11.4 | 1.11 |
| 5 | KOH | 13.0 | 1.20 |

EXAMPLE 14

A series of samples of one of said individual rhodium complex concentrate samples obtained as described in Example 8 above, and containing about 6481 ppm rhodium were heated at about 160° C. for 2, 4, 8, and 16 minutes. An initial unheated sample and each heated sample of said concentrate were then diluted with sufficient triphenylphosphine and Texanol® to produce hydroformylation solutions containing about 300 ppm rhodium and about 5 weight percent triphenylphosphine (about 66 moles of free triphenylphosphine per mole of rhodium). A portion of each solution so prepared was then used to catalyze the hydroformylation of propylene in a stirred autoclave reactor at about 100° C. under about 75 psi. of carbon monoxide, hydrogen and propylene in a 1:1:1 mole ratio. Another portion of each solution so prepared was first washed with a 5 weight percent aqueous solution of sodium bicarbonate and then with water and dried prior to being used in hydroformylating propylene under the same conditions as described above. The relative rate of activity of each sample solution, prior to washing and after washing, is given in Table II below, as compared to the arbitrary relative activity value of 1.00 assigned to said sample solutions derived from the unheated rhodium complex concentrate.

TABLE II

| Time at 160° C. Minutes | Relative Activity Rate Before Wash | Relative Activity Rate After Wash |
|---|---|---|
| 0 | 1.00 | 1.00 |
| 2 | 0.94 | 0.97 |
| 4 | 0.92 | 0.97 |
| 8 | 0.89 | 0.93 |
| 16 | 0.85 | 0.84 |

It should be noted that the concentrates of Examples 2, 7 to 9, 11 and 12 were stored in the presence of air for three to four months before their activity was measured and that it is now considered that the activity values given in said Examples may have benefited at least in part to air being diffused into said concentrates during their preparation and/or their prolonged exposure to air, since subsequent concentrates prepared in a thin film evaporator according to this invention and tested on the same day or soon after preparation were found, when tested in the same manner, to give activity ratings of from about 45 to 55 percent before washing and about 55 to 70 percent after washing as compared to the activity of fresh rhodium complex catalyst.

EXAMPLE 15

A 655 gram sample of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 30 percent of that of fresh catalyst was concentrated in a Arthur F. Smith lab scale thin-film evaporator which was operated at an outer wall temperature of about 141°–155° C. and at 0.4–0.25 mm. Hg. The feed rate was about 546 g./hr. and about 153 grams of an essentially rhodium free distillate consisting essentially of butyraldehyde and other low boiling components was collected overhead. The tails or distillation residue of said first pass consisting of the higher boiling components of the distilled spent medium and essentially all of the rhodium of the original spent feed sample was collected and further concentrated by a second pass through the evaporator at 244°–251° C. and about 0.3 mm. Hg. at a feed rate of about 361 grams/hour. About 492 grams of an essentially rhodium free distillate was collected overhead. In addition a highly viscous rhodium complex concentrate distillation residue was obtained from the bottom of the evaporator which was found to contain about 5672 ppm rhodium and minor amounts of triphenylphosphine, the remainder consisting essentially of triphenylphosphine oxide and higher boiling organic components, e.g. aldehyde pentamers.

On the same day that said rhodium complex concentrate distillation residue containing about 5672 ppm rhodium was prepared a sample of said concentrate was diluted with sufficient triphenylphosphine and sufficient Texanol ®, to produce a brown solution containing about 300 ppm rhodium and about 5 weight percent triphenylphosphine (about 65 moles of free triphenylphosphine per mole of rhodium) and a sample of said solution was then used to catalyze the hydroformylation of propylene in a stirred autoclave reactor at about 100° C. under about 75 psi of carbon monoxide, hydrogen and propylene in a 1:1:1 mole ratio. The activity of the rhodium complex catalyst of said process which employed said concentrate as its source of rhodium was found to be about 34 percent as compared to the activity of fresh rhodium complex catalyst using rhodium dicarbonylacetylacetonate as the source of rhodium for said catalyst under the same conditions.

Again on the same day another sample of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 57 percent as compared to the activity of said fresh rhodium complex catalyst under the same conditions.

Air was then bubbled through another sample of said above rhodium complex concentrate distillation residue containing about 5672 ppm rhodium prepared that same day for 64 hours at room temperature. The air treated sample was then on the same day it was prepared diluted to obtain a light brown solution containing about 300 ppm rhodium and about 5 weight percent triphenylphosphine in the same manner as described above and a sample of said solution prepared from said air treated concentrate was then used to catalyze the hydroformylation of propylene under the same conditions as described above. The activity of the rhodium catalyst which employed said air treated concentrate as its source of rhodium was found to be about 62 percent as compared to the activity of said fresh rhodium complex catalyst under the same conditions.

On the same day another sample solution of said diluted air treated rhodium complex concentrate so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 82 percent as compared to the activity of said fresh rhodium complex catalyst under the same conditions.

By way of comparison a sample of the original spent hydroformylation reaction medium (i.e. original feed material employed in this Example) was used to catalyze the hydroformylation of propylene under the same conditions as described above, as was another sample of said original starting spent hydroformylation medium after it had been washed with said aqueous solution of sodium bicarbonate solution and water and dried in the same manner as described above. The activity of the rhodium complex catalyst using the unwashed sample of spent hydroformylation medium as the source of rhodium for said catalyst was about 30 percent as compared to the activity of said fresh rhodium complex catalyst while the activity of the rhodium complex catalyst using the washed sample of spent hydroformylation medium as the source of rhodium for said catalyst was about 33 percent as compared to the activity of said fresh rhodium complex catalyst.

EXAMPLE 16

A 476 gram sample of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 32 percent of that of fresh catalyst was concentrated in a Arthur F. Smith lab scale thin-film evaporator which was operated at an outer wall temperature of about 150° C. and at about 3 mm. Hg. The spent medium was fed over 90 minutes and about 385 grams of the distillation residue consisting of the higher boiling components of the distilled spent medium and essentially all of the rhodium of the original spent feed sample was collected. About 337 grams of said first pass distillation residue was further concentrated by a second pass through the evaporator at about 230°-245° C. and about 3 mm. Hg. over two hours to yield a highly viscous rhodium complex concentrate distillation residue containing about 6739 ppm rhodium and a minor amount of triphenylphosphine, the remainder consisting essentially of triphenylphosphine oxide and higher boiling organic components, e.g. aldehyde pentamers.

On the same day that said rhodium complex concentrate distillation residue containing about 6739 ppm rhodium was prepared a sample of said concentrate was diluted with sufficient triphenylphosphine and sufficient Texanol ®, to produce a solution containing about 300 ppm rhodium and about 5 weight percent triphenylphosphine (about 65 moles of free triphenylphosphine per mole of rhodium) and a sample of said solution was then used to catalyze the hydroformylation of propylene in a stirred autoclave reactor at about 100° C. under about 75 psi of carbon monoxide, hydrogen and propylene in a 1:1:1 mole ratio. The activity of the rhodium complex catalyst of said process which employed said concentrate as its source of rhodium was found to be about 46 percent as compared to the activity of fresh rhodium complex catalyst using rhodium dicarbonylacetylacetonate as the source of rhodium for said catalyst under the same conditions.

Again on the same day another sample of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 58 percent as compared to the activity of said fresh rhodium complex catlayst under the same conditions.

Two weeks later air was bubbled through another sample of said above rhodium complex concentrate distillation residue containing about 6739 ppm rhodium overnight for 16 hours at 50° C. The air treated sample was then on the same day it was prepared diluted to a solution containing about 300 ppm rhodium and about 5 weight percent triphenylphosphine in the same manner as described above and a sample of said solution prepared from said air treated concentrate was then used to catalyze the hydroformylation of propylene under the same conditions as described above. The activity of the rhodium catalyst which employed said air treated concentrate as its source of rhodium was found to be about 75 percent as compared to the activity of said fresh rhodium complex catalyst under the same conditions. On the same day another sample solution of said diluted air treated rhodium complex concentrate so prepared as described above was first washed with a 5 weight percent solution of sodium bicarbonate and then with water and dried prior to being used in hydroformylating propylene under the same conditions as described above. In this instance the activity of the rhodium complex catalyst was found to have increased to about 86 percent as compared to the activity of said fresh rhodium complex catalyst under the same conditions.

By way of comparison a sample of the original spent hydroformylation reaction medium (i.e. original feed material employed in this Example) was used to catalyze the hydroformylation of propylene under the same conditions as described above, as was another sample of said original starting spent hydroformylation medium after it had been washed with said aqueous solution of sodium bicarbonate and water and dried in the same manner as described above. The activity of the rhodium complex catalyst using the unwashed sample of spent hydroformylation medium as the source of rhodium for said catalyst was about 32 percent as compared to the activity of said fresh rhodium complex catalyst while the activity of the rhodium complex catalyst using the washed sample of spent hydroformylation medium as the source of rhodium for said catalyst was about 40 percent as compared to the activity of said rhodium complex catalyst.

EXAMPLE 17

A 627 gram sample of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 30 percent of that of fresh catalyst was concentrated in a Arthur F. Smith lab scale thin-film evaporator which was operated at an outer wall temperature of about 139°–152° C. and at 0.7–0.8 mm. Hg. The feed rate was about 482 g./hr. and about 159 grams of an essentially rhodium free distillate consisting essentially of butyraldehyde and other low boiling components was collected overhead. The tails or distillation residue of said first pass consisting of the higher boiling components of the distilled spent medium and essentially all of the rhodium of the original spent feed sample was collected and further concentrated by a second pass through the evaporator at 243°–248° C. and about 2.2 mm. Hg. the pressure being maintained by bleeding air into the evaporator while it is in the form of a thin film on the hot walls of the evaporator. A highly viscous rhodium complex concentrate distillation residue was obtained from the bottom of the evaporator which was found to contain about 10,692 ppm rhodium and a minor amount of triphenylphosphine, the remainder consisting essentially of triphenylphosphine oxide and higher boiling organic components, e.g. aldehyde pentamers.

Five days after said air treated rhodium complex concentrate distillation residue containing about 10,692 ppm rhodium was prepared a sample of said concentrate was diluted with sufficient triphenylphosphine and sufficient Texanol ®, to produce a solution containing about 330 ppm rhodium and about 5 weight percent triphenylphosphine (about 60 moles of free triphenylphosphine per mole of rhodium). A sample of said solution was then used to catalyze the hydroformylation of propylene in a stirred autoclave reactor at about 100° C. under about 75 psi of carbon monoxide, hydrogen and propylene in a 1:1:1 mole ratio. The activity of the rhodium complex catalyst of said process which employed said concentrate as its source of rhodium was found to be about 39 percent as compared to the activity of fresh rhodium complex catalyst using rhodium dicarbonylacetylacetonate as the source of rhodium for said catalyst under the same conditions.

Again on the same day another sample of said diluted rhodium complex concentrate solution so prepared as described above was first washed with a 5 weight percent aqueous solution of sodium bicarbonate and then with water and dried prior to being used in hydroformylating propylene under the same conditions as described above. In this instance the activity of the rhodium complex catalyst was found to have increased to about 68 percent as compared to the activity of said fresh rhodium complex catalyst under the same conditions.

EXAMPLE 18

A 55 gallon sample of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, was concentrated in a LUWA 1.4 square foot thin-film evaporator which was operated at an outer wall temperature of about 260°–280° C., 90–94 mm. Hg. and a feed rate of 120–140 lb./hr./ft.$^2$ to remove aldehydes and other low boiling components. The tails or distillation residue of this first pass was then passed through the evaporator a second time at 280°–300° C., 4–9 mm. Hg. and a feed rate of 30–143 lb./hr./ft.$^2$ to remove butyraldehyde diol esters and phosphine compounds. Finally, the tails or distillation residue of said second pass was further concentrated in the evaporator at 305° C., 4 mm. Hg. and a feed rate of 7.4–255 lb./hr./ft.$^2$ to obtain a highly viscous rhodium complex concentrate distillation residue which was found to contain about 9473 ppm rhodium and a minor amount of triphenylphosphine, the remainder consisting essentially of triphenylphosphine oxide and higher boiling organic components e.g. aldehyde pentamers.

A sample of said rhodium complex concentrate distillation residue containing about 9473 ppm rhodium was diluted with sufficient triphenylphosphine and sufficient Texanol ®, to produce a solution containing about 300 ppm rhodium and about 5 weight percent triphenylphosphine (about 65 moles of free triphenylphosphine per mole of rhodium). A sample of said solution was then used to catalyze the hydroformation of propylene in a stirred autoclave reactor at about 100° C. under about 75 psi of carbon monoxide hydrogen and propylene in a 1:1:1 mole ratio. The activity of the rhodium complex catalyst of said process which employed said concentrate as its source of rhodium was found to be about 22 percent as compared to the activity of fresh rhodium complex catalyst using rhodium dicarbonylacetylacetonate as the source of rhodium for said catalyst under the same conditions. It is believed that this low activity rating obtained may have been due in part to the high distillation temperatures employed and the storing of the concentrate in essentially the absence of air for about 8–9 months before testing.

Another sample of said diluted rhodium complex concentrate solution so prepared as described above was first washed with 5 weight percent aqueous solution of sodium bicarbonate and then with water and dried prior to being used in hydroformylating propylene under the same conditions as described above. In this instance the activity of the rhodium complex catalyst was found to have increased to about 46 percent as compared to the activity of said fresh rhodium complex catalyst under the same conditions.

A series of other samples of said above rhodium complex concentrate distillation residue containing about 9473 ppm rhodium were then treated by bubbling air or nitrogen through the concentrate for various periods of time and at various temperatures as outlined in TABLE III below. A portion of each treated sample was then diluted to a solution containing 300 ppm rhodium and about 5 weight percent triphenylphosphine in the same manner as described above and a portion of each solution then used to catalyze the hydroformylation of propylene under the same conditions given above. Another portion of each solution so prepared was first washed with a 5 weight percent aqueous sodium bicarbonate solution and water in the same manner as described above prior to being used in hydroformylating propylene under the same conditions described above. The activity of the rhodium catalyst which employed said gas treated concentrates as its source of rhodium as compared to the activity of said fresh rhodium complex catalyst is given in Table III below.

TABLE III

| | | | | Activity (%) | |
|---|---|---|---|---|---|
| Sample | Treatment | Temp. | Time | Before Wash | After Wash |
| A | Air | 50° C. | 16 hrs. | 48 | 65 |
| B | Air | 25° C. | 16 hrs. | 39 | 48 |
| C | Air | 100° C. | 24 hrs. | 56 | 68 |
| D | Nitrogen | 50° C. | 60 hrs. | 25 | 38 |

EXAMPLE 19

A 4997 pound sample of a spent hydroformylation reaction medium obtained from a continuous hydroformylation process of propylene with carbon monoxide and hydrogen to produce butyraldehyde in the presence of a rhodium complex catalyst consisting essentially of rhodium complexed with carbon monoxide and triphenylphosphine, and free triphenylphosphine, said medium containing less than 400 ppm rhodium, and whose catalytic activity had declined to about 30 percent of that of fresh catalyst was concentrated in through a Pfaudler 13.4 square foot thin-film evaporator which was operated at an outer wall temperature of about 187° C., about 150 mm. Hg. and a feed rate of about 416 lbs./hr. to remove aldehydes and other low boiling components. The tails or distillation residue of this first pass was then passed through the evaporator a second time at about 237° C., about 66 mm. Hg. and a feed rate of about 296 pounds per hour to remove butyraldehyde diol esters and phosphine compounds. The tails or distillation concentrate residue of said second pass were collected and found to contain 17.7 percent of the original spent hydroformylation medium feed material and 98.4 percent (1560 ppm rhodium) of the rhodium of said original feed material. A sample of this second pass distillation residue was set aside while the remainder of said residue of said second pass was further concentrated by passing it through the evaporator at about 272° C., about 3 mm. Hg. and a feed rate of about 195 pounds per hour to obtain a final viscous rhodium complex concentrate distillation residue containing 2.3 percent of the original spent hydroformylation medium feed material and 79 percent (8329 ppm rhodium) of the rhodium of said original feed material.

Samples of said rhodium complex concentrate distillation residues obtained from pass two (1560 ppm rhodium) and pass three (8329 ppm rhodium) above, were oxygenated by stirring each sample concentrate under a pressure of about 100 psi. of air for 16 hours at room temperature. Each oxygenated sample concentrate as well as samples of each non-oxygenated sample concentrate were diluted with sufficient triphenylphosphine and sufficient Texanol ® to produce a solution containing about 200 ppm rhodium and 12 weight percent triphenylphosphine. A portion of each oxygenated solution so prepared was then washed with a 10 weight percent aqueous sodium bicarbonate solution and water. Each sample solution both before washing and after washing was then used to catalyze the hydroformylation of propylene in a continuous reactor at about 105° C. under carbon monoxide, hydrogen and propylene.

This same hydroformylation procedure was also carried out using the original spent hydroformylation reaction medium (i.e. the original feed employed in this Example) after it was washed with 10 weight percent sodium bicarbonate and water.

The catalytic activity or butyraldehyde production measured as gram-moles of butyraldehydes per liter of solution per hour, for each solution was measured and was compared to the activity of a fresh rhodium complex catalyst under the same conditions. The results of this Example are given in Table IV below.

TABLE IV

| Sample No. | Catalyst Source | Air Treatment | Wash Treatment | Duration of Activity Test (Days) | Catalyst Activity |
|---|---|---|---|---|---|
| A | Spent Hydroformylation feed | No | Yes | 12 | 38% |
| B | Second Pass Concentrate | No | No | 18 | 59% |
| C | Second Pass Concentrate | Yes | No | 18 | 74% |
| D | Second Pass Concentrate | Yes | Yes | 18 | 73% |
| E | Third Pass Concentrate | No | No | 18 | 46% |
| F | Third Pass Concentrate | Yes | No | 18 | 63% |
| G | Third Pass Concentrate | Yes | Yes | 18 | 82% |

EXAMPLE 20

Samples of said rhodium complex concentrate distillation residues obtained from pass two (1560 ppm rhodium) and pass three (8329 ppm rhodium) of Example 19 were each diluted with sufficient Texanol ® to give solutions containing about 300 ppm rhodium and and stirred in the presence of air under atmospheric conditions. Samples of each solution were withdrawn periodically and sufficient triphenylphosphine added to each sample to obtain a hydroformylation medium containing 10 weight percent triphenylphosphine. The hydroformylation medium both before and after having been washed with a 10 weight percent aqueous sodium bicarbonate solution and water was then used to catalyze the hydroformylation of propylene in the same manner as described in Example 17. The activity of the rhodium catalyst which employed said concentrates as its source of rhodium was compared to the activity of fresh rhodium complex catalyst using rhodium dicarbonylacetylacetonate as the source of rhodium for said catalyst under the same conditions. The results of this Example are given in Table V below.

TABLE V

| Sample No. | Catalyst Source | Days of Air Treatment | Wash Treatment | Catalyst Activity (%) |
|---|---|---|---|---|
| A | Second Pass Concentrate | 0 | No | 52 |
| B | Second Pass Concentrate | 1 | No | 65 |
| C | Second Pass Concentrate | 2 | No | 60 |
| D | Second Pass Concentrate | 5 | No | 67 |
| E | Second Pass Concentrate | 5 | Yes | 71 |
| F | Second Pass Concentrate | 8 | No | 62 |
| G | Second Pass Concentrate | 8 | Yes | 74 |
| H | Third Pass Concentrate | 0 | No | 57 |
| I | Third Pass Concentrate | 1 | No | 65 |
| J | Third Pass Concentrate | 2 | No | 63 |
| K | Third Pass Concentrate | 5 | No | 62 |
| L | Third Pass Concentrate | 5 | Yes | 78 |
| M | Third Pass Concentrate | 8 | No | 73 |
| N | Third Pass Concentrate | 8 | Yes | 75 |

EXAMPLE 21

A 2.11 gram sample of a rhodium complex concentrate distillation residue obtained as described in Example 18 and containing about 14,200 ppm rhodium was diluted with 102 ml. of Texanol ® and mixed with 1.31 grams of tertbutylhydroperoxide at 95° C. for four hours. Then a 31.8 gram sample of the solution so prepared was mixed with 3.8 grams of triphenylphosphine and 2.5 grams of additional Texanol ® and stirred at 95° C. for an additional hour. This final solution was then washed with two equivalent volumes of 10 weight percent aqueous sodium bicarbonate solution and then with 35 ml. of water. The solution obtained after said wash treatment contained 252 ppm rhodium and 9 weight percent triphenylphosphine and was then used to catalyze the hydroformylation of propylene in the same manner as described in Example 17. The activity of the rhodium catalyst which employed said rhodium complex concentrate as its source of rhodium was 83 percent as compared to the activity of fresh rhodium complex catalyst using rhodium dicarbonylacetylacetonate as the source of rhodium for said catalyst under the same conditions.

Various modifications and variations of this invention will be obvious to a worker skilled in the art and it is to be understood that such modifications and variations are to be included within the purview of this application and the spirit and scope of the appended claims.

What is claimed is:

1. A process for preparing a hydroformylation medium, said medium comprising a rhodium complex and triarylphosphine, which comprises mixing a rhodium complex concentrate with a sufficient amount of triarylphosphine so that there is at least about 10 moles of free triarylphosphine per mole of rhodium present in said medium; said rhodium complex concentrate having been produced by a process which comprises concentrating a spent hydroformylation reaction medium that contains a partially deactivated rhodium complex catalyst, free triarylphosphine, aldehyde products and higher boiling aldehyde condensation by-products, into at least two separate material streams so as to remove free triarylphosphine, aldehyde products and higher boiling aldehyde condensation by-products from said spent hydroformylation reaction medium by means of distillation at temperatures of about 20° C. to about 350° C. and at pressures of about 1000 mm Hg. to about $1 \times 10^{-6}$ mm Hg., wherein one stream is said rhodium complex concentrate distillation residue containing a major amount of the rhodium of said catalyst and which has been concentrated to about 0.1 to about 30 percent by weight of said spent hydroformylation reaction medium, and the other material stream or streams consist essentially of one or more of the distilled volatile components of said spent hydroformylation reaction medium.

2. A process as defined in claim 1, wherein said concentrate contains more than about 90 percent by weight of all of the rhodium of said partially deactivated catalyst.

3. A process as defined in claim 1, wherein said concentrate contains more than about 97 percent by weight of all of rhodium of said partially deactivated catalyst.

4. A process as defined in claim 1, wherein the distillation takes place in two stages and wherein the second distillation stage is distilled at a lower pressure than the first distillation stage.

5. A process as defined in claim 4, wherein the first distillation stage is conducted at temperatures of about 20° C. to about 250° C. and pressures of about 1000 mm Hg. to about 0.1 mm Hg., and the second distillation stage is conducted at temperatures of about 25° C. to about 350° C. and pressures of about 100 mm Hg. to about $1 \times 10^{-6}$ mm Hg.

6. A process as defined in claim 5, wherein the first distillation stage is conducted at temperatures of about 20° C. to about 190° C. and pressures of about 150 mm Hg. to about 0.5 mm Hg., and the second distillation stage is conducted at temperatures of about 150° C. to about 300° C. and pressure of about 20 mm Hg. to about 0.1 mm Hg.

7. A process as defined in claim 1, wherein the spent hydroformylation reaction medium is batch distilled.

8. A process as defined in claim 1, wherein the distillation is carried out in a thin-film evaporator.

9. A process as defined in claim 1, wherein sufficient triarylphosphine and sufficient solvent has been mixed with said concentrate so that the hydroformylation medium contains at least about 50 moles of free triarylphosphine per mole of rhodium and from about 25 to about 1000 ppm rhodium calculated as free metal.

10. A process as defined in claim 9, wherein the hydroformylation medium contains from about 50 to about 400 ppm rhodium calculated as free metal and wherein the triarylphosphine is triphenylphosphine.

11. A process as defined in claim 10, wherein the solvent is selected from the group consisting of aldehydes and higher boiling aldehyde condensation products.

12. A process as defined in claim 4, wherein said rhodium complex concentrate has been concentrated to about 2 to about 6 percent by weight of said spent hydroformylation reaction medium.

13. A process as defined in claim 1, wherein the process for producing said rhodium complex concentrate also involves washing the rhodium complex concentrate with an aqueous alkaline solution and/or water.

14. A process as defined in claim 1, wherein the process for producing said rhodium complex concentrate also involves adding an oxidant selected from the group consisting of oxygen and an organic peroxide to the rhodium complex concentrate.

15. A process as defined in claim 14, wherein the oxidant is oxygen.

16. A process as defined in claim 15, wherein said oxidant is oxygen in the form of air which has been thoroughly dispersed throughout said concentrate by directly feeding air into said rhodium complex concentrate distillation residue.

17. A process as defined in claim 14, wherein the process for producing said rhodium complex concentrate also involves washing the oxidant treated rhodium complex concentrate with an aqueous alkaline solution and/or water.

18. A process as defined in claim 5, wherein the process for producing said rhodium complex concentrate also involves washing the rhodium complex concentrate with an aqueous alkaline solution and/or water.

19. A process as defined in claim 5, wherein the process for producing said rhodium complex concentrate also involves adding an oxidant selected from the group consisting of oxygen and an organic peroxide to the rhodium complex concentrate.

20. A process as defined in claim 19, wherein the oxidant is oxygen.

21. A process as defined in claim 20, wherein said oxidant is oxygen in the form of air which has been thoroughly dispersed throughout said concentrate by directly feeding air into said rhodium complex concentrate distillation residue.

22. A process as defined in claim 19, wherein the process for producing said rhodium complex concentrate also involves washing the oxidant treated rhodium complex concentrate with an aqueous alkaline solution and/or water.

23. A process as defined in claim 19, wherein the first distillation stage is batch distilled and the second distillation stage is carried out in a thin-film evaporator.

24. A process as defined in claim 19, wherein both distillation stages are carried out in a thin-film evaporator.

25. A process as defined in claim 24, wherein both distillation stages are carried out in a wiped-film evaporator.

26. A process as defined in claim 19, wherein the rhodium complex concentrate has been concentrated to about 1 to about 10 percent by weight of said spent hydroformylation reaction medium.

27. A process as defined in claim 26, wherein the triarylphosphine is triphenylphosphine and wherein said rhodium complex concentrate consists essentially of from about 1000 to about 50,000 ppm of rhodium calculated as free metal, and less than 10 percent by weight of triphenylphosphine based on the total weight of the concentrate, the remainder consisting essentially of higher boiling aldehyde condensation by-products and phosphine oxides.

28. A hydroformylation medium comprising a rhodium complex and at least about 10 moles of free triarylphosphine per mole of rhodium present in said medium, said rhodium complex having been derived from a rhodium complex concentrate which has been produced by a process which comprises concentrating a spent hydroformylation reaction medium that contains a partially deactivated rhodium complex catalyst, free triarylphosphine, aldehyde products and higher boiling aldehyde condensation by-products, into at least two separate material streams so as to remove free triarylphosphine, aldehyde products and higher boiling aldehyde condensation by-products from said spent hydroformylation reaction medium by means of distillation at temperatures of about 20° C. to about 350° C. and at pressures of about 1000 mm Hg. to about $1 \times 10^{-6}$ mm Hg., wherein one stream is said rhodium complex concentrate distillation residue containing a major amount of the rhodium of said catalyst and which has been concentrated to about 0.1 to about 30 percent by weight of said spent hydroformylation reaction medium, and the other material stream or streams consist essentially of one or more of the distilled volatile components of said spent hydroformylation reaction medium.

29. A hydroformylation medium as defined in claim 28, wherein said concentrate contains more than about 90 percent by weight of all of the rhodium of said partially deactivated catalyst.

30. A hydroformylation medium as defined in claim 28, wherein said concentrate contains more than about 97 percent by weight of all of the rhodium of said partially deactivated catalyst.

31. A hydroformylation medium as defined in claim 28, wherein the distillation takes place in two stages and wherein the second distillation stage is distilled at a lower pressure than the first distillation stage.

32. A hydroformylation medium as defined in claim 31, wherein the first distillation stage is conducted at temperatures of about 20° C. to about 250° C. and pressures of about 1000 mm Hg. to about 0.1 mm Hg., and the second distillation stage is conducted at temperatures of about 25° C. to about 350° C. and pressures of about 100 mm Hg. to about $1 \times 10^{-6}$ mm Hg.

33. A hydroformylation medium as defined in claim 32, wherein the first distillation stage is conducted at temperatures of about 20° C. to about 190° C. and pressures of about 150 mm Hg. to about 0.5 mm Hg., and the second distillation stage is conducted at temperatures of about 150° C. to about 300° C. and pressures of about 20 mm Hg. to about 0.1 mm. Hg.

34. A hydroformylation medium as defined in claim 28, wherein the spent hydroformylation reaction medium is batch distilled.

35. A hydroformylation medium as defined in claim 28, wherein the distillation is carried out in a thin-film evaporator.

36. A hydroformylation medium as defined in claim 28, wherein said hydroformylation medium contains at least about 50 moles of free triarylphosphine per mole of rhodium, and wherein said hydroformylation medium also contains a solvent for said rhodium complex and from about 25 to about 1000 ppm rhodium calculated as free metal.

37. A hydroformylation medium as defined in claim 36, wherein said hydroformylation medium contains from about 50 to about 400 ppm rhodium calculated as free metal and wherein the triarylphosphine is triphenylphosphine.

38. A hydroformylation medium as defined in claim 37, wherein the solvent is selected from the group consisting of aldehydes and higher boiling aldehyde condensation products.

39. A hydroformylation medium as defined in claim 31, wherein said rhodium complex concentrate has been concentrated to about 2 to about 6 percent by weight of said spent hydroformylation reaction medium.

40. A hydroformylation medium as defined in claim 31, wherein both distillation stages are carried out in a wiped-film evaporator.

41. A hydroformylation medium as defined in claim 28, wherein the process for producing said rhodium complex concentrate also involves washing the rhodium complex concentrate with an aqueous alkaline solution and/or water.

42. A hydroformylation medium as defined in claim 28, wherein the process for producing said rhodium complex concentrate also involves adding an oxidant selected from the group consisting of oxygen and an organic peroxide to the rhodium complex concentrate.

43. A hydroformylation medium as defined in claim 42, wherein the oxidant is oxygen.

44. A hydroformylation medium as defined in claim 43, wherein said oxidant is oxygen in the form of air which has been thoroughly dispersed throughout said concentrate by directly feeding air into said rhodium complex concentrate distillation residue.

45. A hydroformylation medium as defined in claim 42, wherein the process for producing said rhodium complex concentrate also involves washing the rhodium complex concentrate with an aqueous alkaline solution and/or water.

46. A hydroformylation medium as defined in claim 32, wherein the process for producing said rhodium complex concentrate also involves washing the rhodium complex concentrate with an aqueous alkaline solution and/or water.

47. A hydroformylation medium as defined in claim 32, wherein the process for producing said rhodium complex concentrate also involves adding an oxidant selected from the group consisting of oxygen and an organic peroxide to the rhodium complex concentrate.

48. A hydroformylation medium as defined in claim 47, wherein the oxidant is oxygen.

49. A hydroformylation medium as defined in claim 48, wherein said oxidant is oxygen in the form of air which has been thoroughly dispersed throughout said concentrate by directly feeding air into said rhodium complex concentrate distillation residue.

50. A hydroformylation medium as defined in claim 47, wherein the process for producing said rhodium complex concentrate also involves washing the oxidant treated rhodium complex concentrate with an aqueous alkaline solution and/or water.

51. A hydroformylation medium as defined in claim 47, wherein the first distillation stage is batch distilled and the second distillation stage is carried out in a thin-film evaporator.

52. A hydroformylation medium as defined in claim 47, wherein both distillation stages are carried out in a thin-film evaporator.

53. A hydroformylation medium as defined in claim 47, wherein the rhodium complex concentrate has been concentrated to about 1 to about 10 percent by weight of said spent hydroformylation reaction medium.

54. A hydroformylation medium as defined in claim 53, wherein the triarylphosphine is triphenylphosphine and wherein said rhodium complex concentrate consists essentially of from about 1000 to about 50,000 ppm of rhodium calculated as free metal, and less than 10 percent by weight of triphenylphosphine based on the total weight of the concentrate, the remainder consisting essentially of higher boiling aldehyde condensation by-products and phosphine oxides.

* * * * *